(12) United States Patent
Tasch et al.

(10) Patent No.: US 11,684,288 B2
(45) Date of Patent: *Jun. 27, 2023

(54) MULTIDIMENSIONAL ACCELERATION AND/OR FORCE GAIT ANALYSIS SYSTEM FOR DIAGNOSIS

(71) Applicant: STEP ANALYSIS LLC, Baltimore, MD (US)

(72) Inventors: Uri Tasch, Baltimore, MD (US); Jason Dunthorn, Baltimore, MD (US)

(73) Assignee: STEP ANALYSIS LLC, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/858,501

(22) Filed: Jul. 6, 2022

(65) Prior Publication Data

US 2022/0330849 A1 Oct. 20, 2022

Related U.S. Application Data

(63) Continuation of application No. 16/606,031, filed as application No. PCT/US2018/027006 on Apr. 11, 2018, now Pat. No. 11,406,282.

(60) Provisional application No. 62/487,944, filed on Apr. 20, 2017.

(51) Int. Cl.
*A61B 5/103* (2006.01)
*A61B 5/11* (2006.01)
*A61B 5/00* (2006.01)

(52) U.S. Cl.
CPC ............ *A61B 5/1036* (2013.01); *A61B 5/112* (2013.01); *A61B 5/4082* (2013.01); *A61B 2562/0219* (2013.01); *A61B 2562/0247* (2013.01); *A61B 2562/0252* (2013.01)

(58) Field of Classification Search
CPC ..... A61B 5/1036; A61B 5/112; A61B 5/4082; A61B 2562/0219; A61B 2562/0247; A61B 2562/0252
See application file for complete search history.

(56) References Cited

U.S. PATENT DOCUMENTS

| | | | | |
|---|---|---|---|---|
| 4,658,923 A | * | 4/1987 | Labarile | G01G 21/12 177/255 |
| 2010/0217157 A1 | * | 8/2010 | Tasch | A61B 5/0036 600/592 |
| 2012/0266648 A1 | * | 10/2012 | Berme | A61B 5/1112 73/862.041 |

* cited by examiner

*Primary Examiner* — Patrick Fernandes
*Assistant Examiner* — Anna Roberts
(74) *Attorney, Agent, or Firm* — WCF IP

(57) ABSTRACT

Disclosed herein is a gait analysis apparatus that is configured to provide multidimensional measures of the gait of an individual as the individual traverses the gait analysis apparatus. The gait analysis apparatus may be configured to provide a gait measuring processing device with the multidimensional measurements. Based on the multidimensional measurements, the gait measuring process device may, for example, diagnose the test subject with lameness or particular neuromuscular dysfunctions (NM) disease and/or injury, monitor progression of lameness or a particular NM disease and/or injury over time, determine a static weight as the test subject is traversing, monitor the static weight of the test subject over an extended period time, and/or determine which measurements may be used as biomarkers to identify lameness or the particular NM disease and/or injury. A system including a gait analysis apparatus is also disclosed.

20 Claims, 11 Drawing Sheets

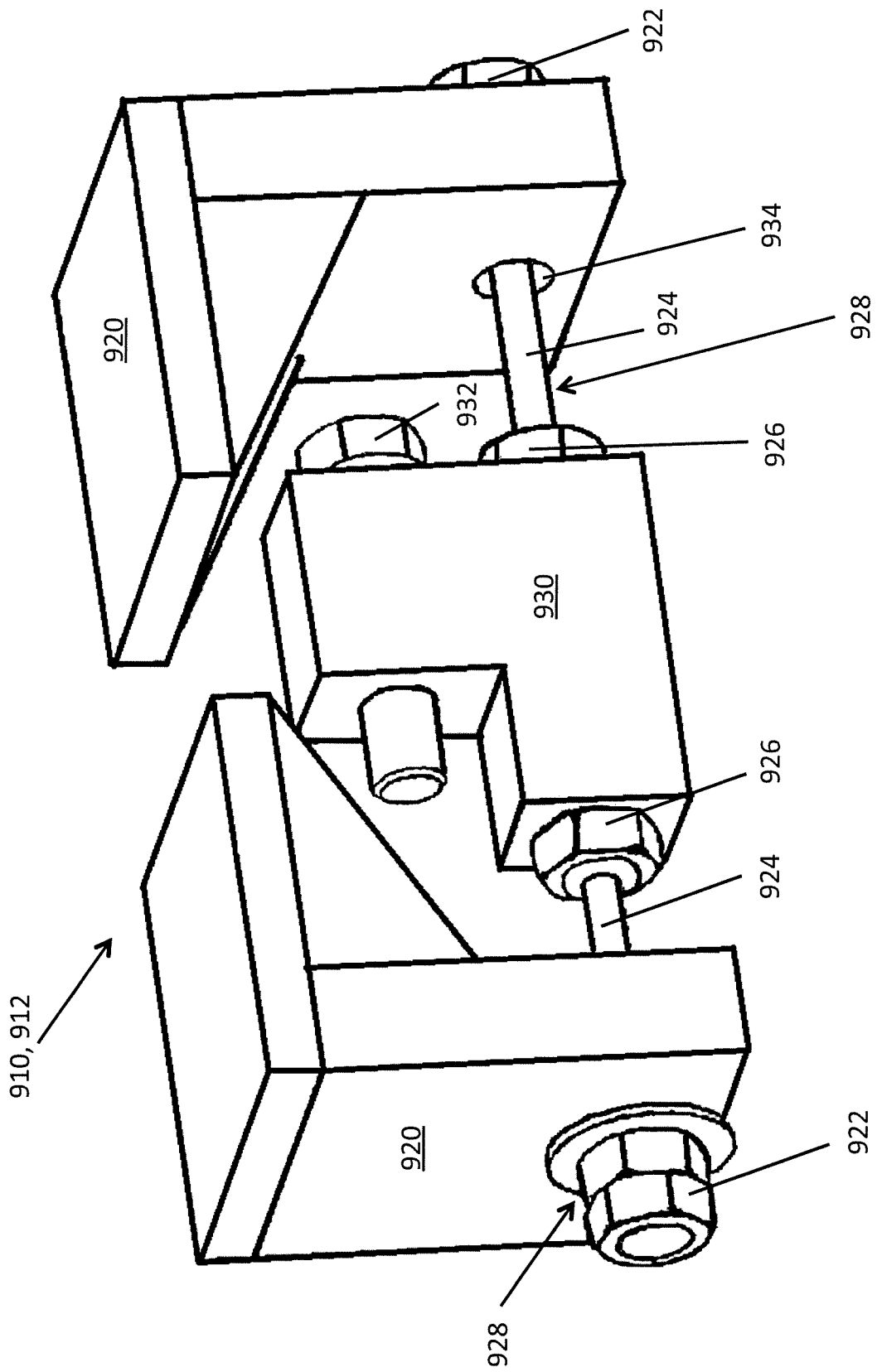

MULTIDIMENSIONAL ACCELERATION AND/OR FORCE GAIT ANALYSIS SYSTEM FOR DIAGNOSIS

CROSS-REFERENCE TO RELATED APPLICATIONS

This applications claims priority and benefit under 35 U.S.C. § 119(e) to U.S. Provisional Patent Application No. 62/487,944, entitled "Multidimensional Acceleration and/or Force Gait Analysis System for Diagnosis", filed on Apr. 20, 2017. The content of that application is incorporated herein in its entirety by reference.

BACKGROUND OF THE INVENTION

Dairy production is an important industry in the U.S. and a major branch of agriculture in many countries around the world. Bovine lameness caused by hoof and leg ailments is a costly problem for the dairy farmer. Lameness necessitates medical treatment, reduces milk production, results in decreased body condition, impairs reproduction performance, and adversely impacts the social status of animals. Milk production is reduced beginning as early as 4 months prior to detection of clinical lameness. Further, milk production rates tend to worsen as lameness severity increases creating a need for early detection.

According to the U.S. Department of Agriculture, rates of lameness continue to be on the rise. Research conducted to establish lameness prevalence in high-producing areas of North America found the prevalence of lameness to be (mean±SD) 30.8%±15.5% in California, 54.8%±16.7% in the northeastern United States, and 27.9%±14.1% in British Columbia. Though the actual rate of lameness is difficult to identify, which is mainly because of the inadequate current methods of diagnosis, its prevalence is significant and is on the rise suggesting deterioration in hoof and leg health for dairy cattle worldwide.

Lameness in dairy cattle increasingly burdens producers as a costly animal welfare and production problem, imparting a large financial toll on the dairy industry. Losses in the form of treatment costs, decreased fertility rates, involuntary culling rates, and lost milk production increase as lameness severity increases. As rates of lameness increase, the dairy industry has brought more attention to the need for early and accurate lameness detection. Economically, assuming the U.S.D.A.'s conservative estimate of 14% lameness prevalence across the 9.1 million adult dairy cows in the U.S., the annual financial loss due to lameness in the U.S. is over $500 million. These losses significantly impair dairy farms and harm the entire industry.

Lameness in dairy herds has been reported to be a critical economic factor and a vital animal-welfare issue for the dairy industry around the world. Other agriculture industries are also affected by lameness, including, among others, horses, beef cattle, sheep and swine. Oftentimes, early diagnosis of such disease or injury can be useful in early treatment therapies. Furthermore, monitoring disease progression by observing changes to the gait of the individual over time, for example, may provide data that may be used to evaluate treatments such as drug therapies, physical therapies, and others.

Various lameness evaluation schemes that assess the severity of the lameness have been suggested. These schemes are based on visual observations of individual cattle. In one scheme, lameness scoring is based on the shape of the cow's back both as the animal stands and as the animal walks. However, this scheme is highly labor intensive, and its results are highly subjective, non-repeatable and non-quantitative in nature.

Methods as disclosed in Pastell, M., et al. (2009) are limited to using accelerometers attached to the limbs of dairy cows. While initial academic research has shown some promise, the cost and ineffectiveness of attaching accelerometers to each limb of every cow in the herd hinders any commercial application for daily farm operations. Further, such an arrangement suffers from a number of flaws, including but not limited to breaking and/or removal of the accelerometers by the cows kicking the accelerometers against gates or other pieces of equipment on the farm and/or laying on them.

Similarly, existing systems have limitations in their ability to diagnose and/or to monitor a Neuromuscular (NM) disease or injury in humans and animals (e.g. cows, horses, rodents). According to the ALS Association, an average of 5,600 people are diagnosed with ALS each year, and currently about 30,000 Americans may be affected. The average life expectancy of a person suffering from ALS is two to five years from the time of diagnosis. Further, the Parkinson's Disease Foundation reports that approximately one million Americans and an estimated seven to ten million people worldwide currently suffer from Parkinson's disease. Although Parkinson's disease itself is not fatal, it greatly reduces one's quality of life and may lead to complications that can reduce life expectancy.

In particular, diagnosis of such diseases is challenging, because, for example, the epidemiology of certain NM diseases or injury may not be known. Furthermore, monitoring changes to the gait of the individual may not be possible from a visual inspection of the individual's gait. In addition, existing systems do not adequately identify various parameters related to the gait of the individual that may be used to diagnose and monitor NM disease or injury. Accordingly, the prior art fails to overcome these shortcomings as well as other drawbacks exist.

SUMMARY OF THE INVENTION

According to various embodiments of the disclosure, the system may include a gait analysis apparatus that is configured to provide multidimensional measures of the gait of an individual as the individual (hereinafter "test subject") traverses the gait analysis apparatus. The gait analysis apparatus may be configured to provide a gait measuring processing device with the multidimensional measurements. Based on the multidimensional measurements, the gait measuring process device may, for example, diagnose the test subject with lameness or particular Neuromuscular (NM) dysfunctions disease and/or injury, monitor progression of lameness or a particular NM disease and/or injury over time, determine a static weight as the test subject is traversing, monitor the static weight of the test subject over an extended period time, and/or determine which measurements may be used as biomarkers to identify lameness or the particular NM disease and/or injury.

As depicted by various exemplary embodiments of the invention, the gait analysis apparatus is a dual-sensor system configured with the gait measuring processing device to determine, model and/or analyze locomotion parameters based on the robust measurements measured by both load cells and accelerometers in order to monitor and/or diagnose test subjects with lameness and/or various NM diseases and/or injury. In one exemplary embodiment, each of the load sensors may be replaced with a simple inexpensive restriction block such that the invention merely functions with the use of inexpensive accelerometers, reducing the manufacturing costs as well as providing a more reliable gait analysis apparatus. Various embodiments of the disclosure further provide the gait analysis apparatus includes a suspended sensor region to negate any friction forces interfering with accurate measurement of the gait of a test subject traversing the gait analysis apparatus. For example, the sensor region may be suspended in one or all of the directions, bolstering the accuracy of the data collection by the gait analysis apparatus.

Various other objects, features, and advantages of the invention will be apparent through the detailed description of the preferred embodiments and the drawings attached hereto. It is also to be understood that both the foregoing general description and the following detailed description are exemplary and not restrictive of the scope of the invention.

BRIEF OF DESCRIPTION OF THE DRAWINGS

Figure 8A:
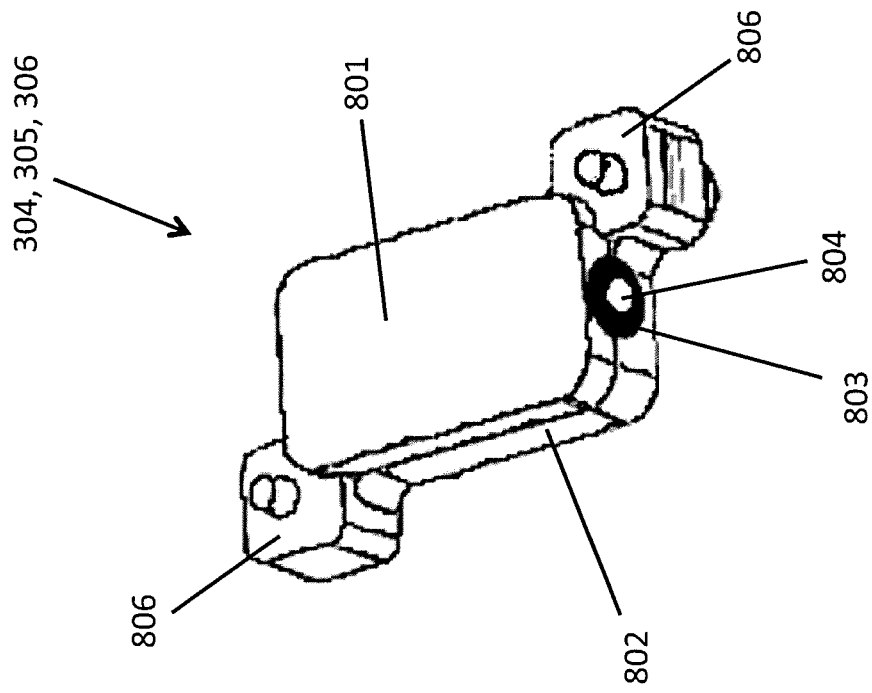
Figure 8B:
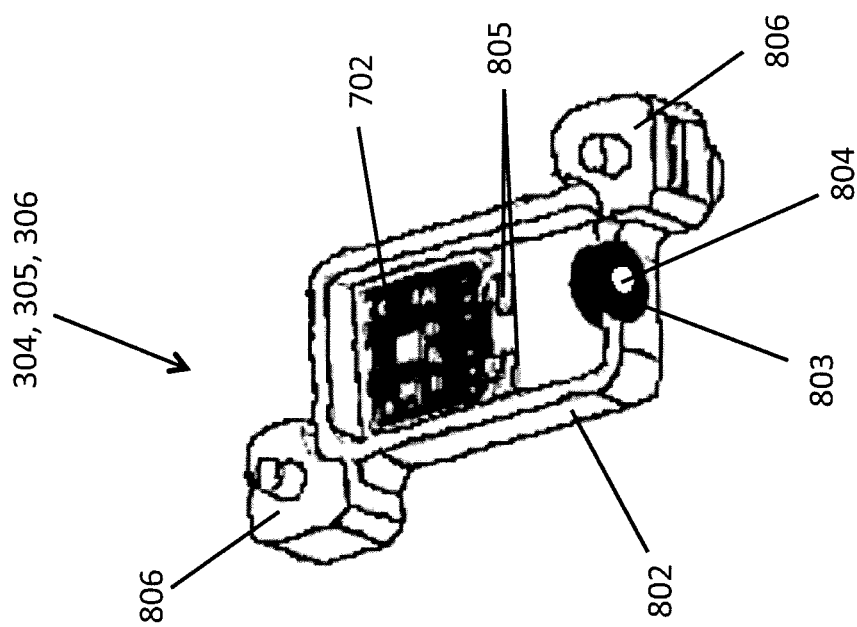

FIGS. 8(a) and 8(b) are illustrations of another example of the acceleration sensor modules according to an embodiment of the disclosed invention.

Figure 9:
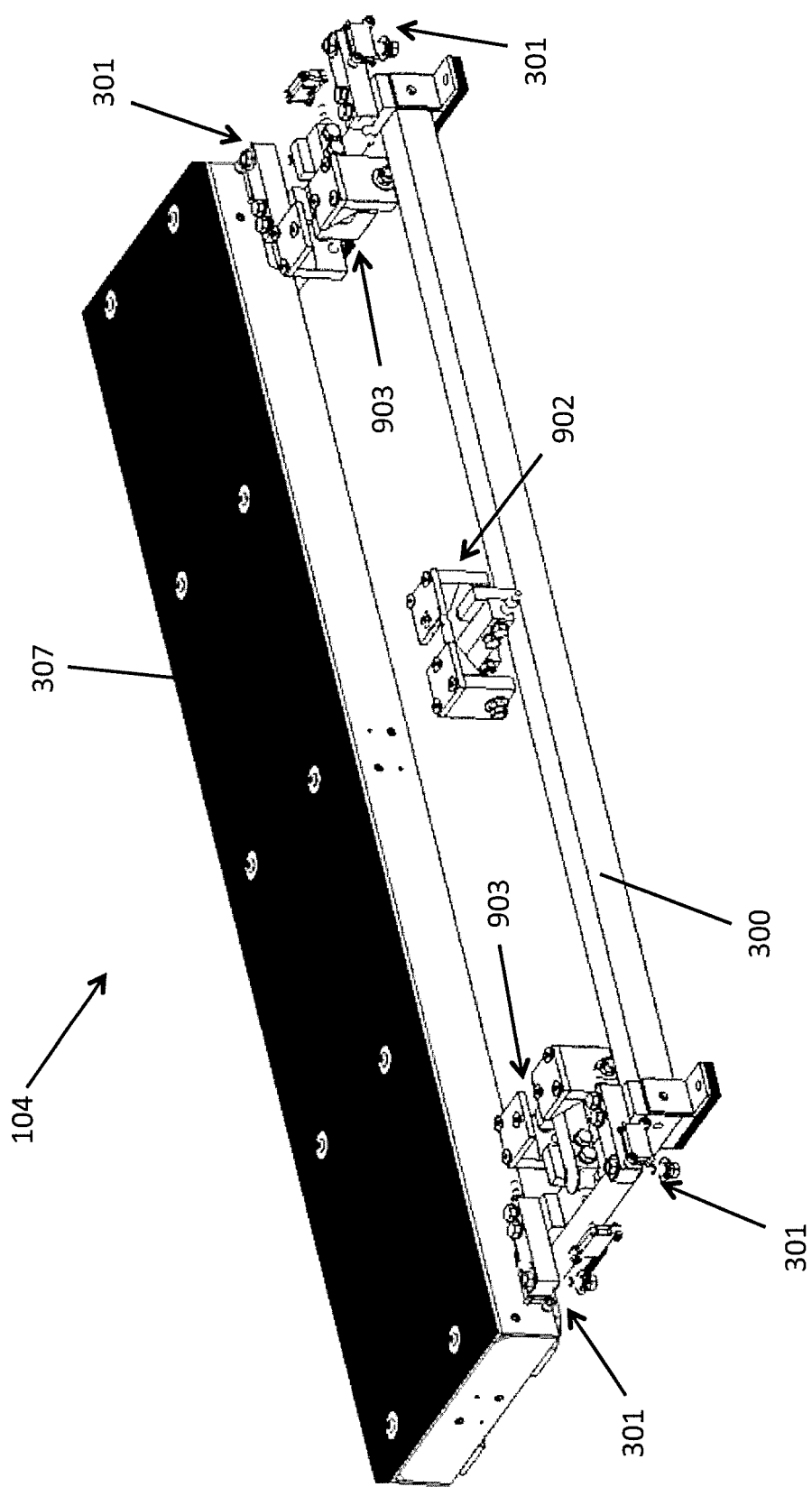

FIG. 9 provides a second exemplary embodiment of the invention showing a sensor region suspended in all three directions.

Figure 10:
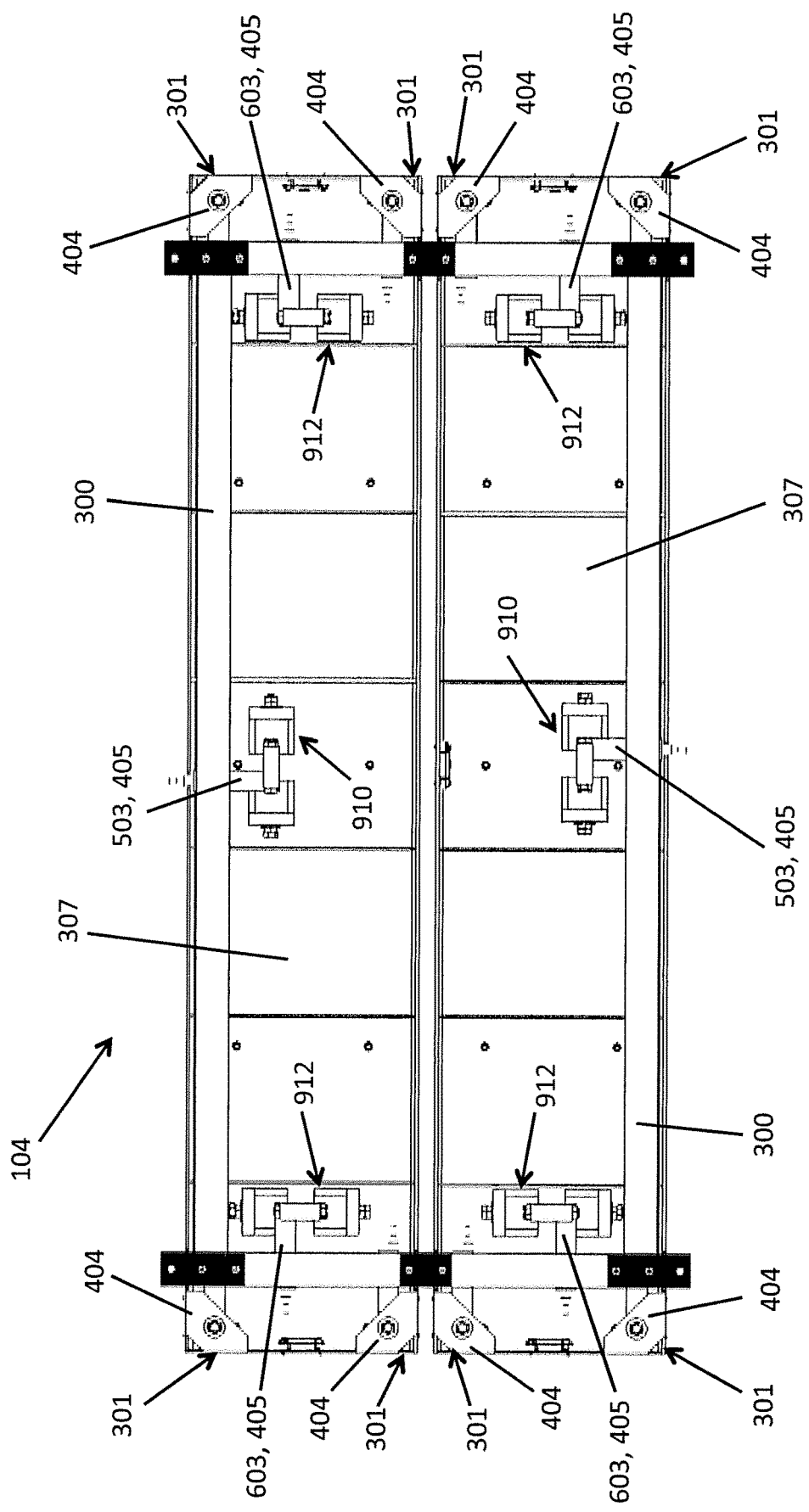

FIG. 10 depicts the bottom view of the sensor region according to the second exemplary embodiment of the invention.

FIG. 11 shows one example of a suspension assembly according to the second exemplary embodiment of the invention.

DETAILED DESCRIPTION OF THE DISCLOSURE

Embodiments of the invention relate to novel methods and apparatuses for diagnosing diseases or injuries that may impair or otherwise alter the gait (e.g., locomotion) of a suffering individual (i.e., human or animal). For example, embodiments of the invention may detect lameness and Neuromuscular (NM) dysfunctions or diseases, such as, but not limited to, Amyotrophic Lateral Sclerosis (ALS; commonly, "Lou Gehrig's disease"), and Parkinson's disease, promoting both human and animal well-being.

Figure 1:
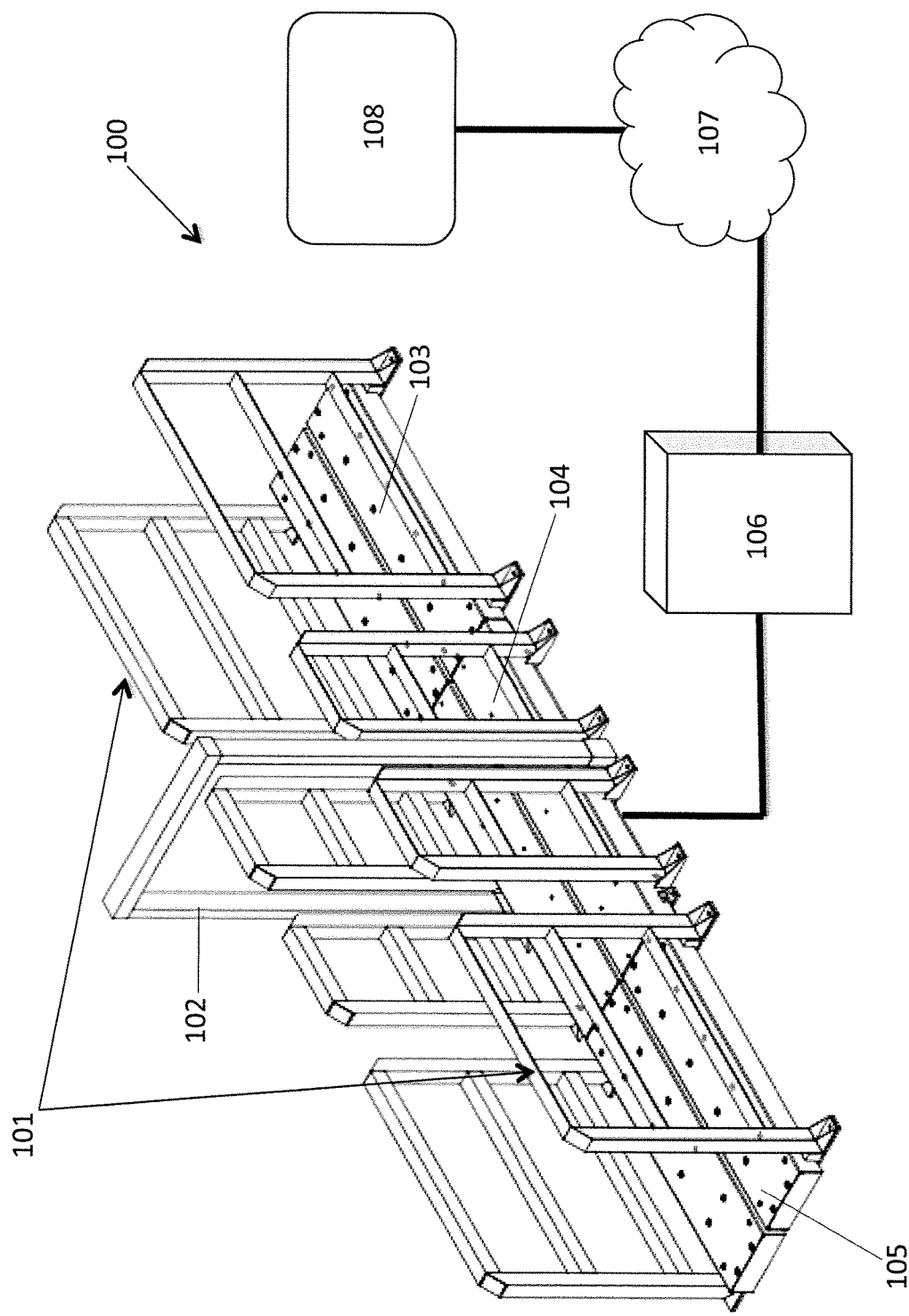
FIG. 1 is an illustration of an example gait analysis apparatus for gait analysis, monitoring and diagnosis according to one embodiment of the disclosure.

FIG. 1 is an illustration of an example gait analysis apparatus 100 for gait analysis and diagnosis according to an embodiment of the disclosure. The gait analysis apparatus 100 may include side railings 101, identification antenna 102, entry region 103, sensor region 104, exit region 105, gait measuring processing device 106, network 107 and output device 108. As the gait analysis apparatus 100 is traversed by the test subject (i.e., human or animal), the gait analysis apparatus 100 measures, among many other variables, the forces (or loads) and accelerations in multiple dimensions related to walking gait of a test subject resulting from the traversal. For example, the multiple dimensions may include acceleration, force, time, magnitude, frequency and special variables.

Particularly for herd animals, the gait analysis apparatus 100 has a walk-through layout configured to guide each of the test subjects (e.g., humans or animals) through the sensor region 104. The gait analysis apparatus 100 is particularly suited to applications wherein a plurality of animals, such as a herd of cattle, are to sequentially enter the system to determine the presence of lameness or other dysfunction that impairs the test subject's gait in any particular individual in the group.

To ensure a test subject traverses the system properly, impediments to a traversing test subject's movements may be provided. For example, one impediment may be to restrict the width of the sensor region in accordance with the size of the test subject. Other possible impediments that may be implemented are disclosed in U.S. Pat. No. 6,699,207, entitled "Method and Apparatus for Detecting Lameness in Animals," and which is fully and expressly incorporated herein by reference. By way of example, possible impediments may include side railings 101 and a partition or divider. The side railings 101 constrain the test subject's lateral movement to thereby force the test subject to walk over the sensor region 104.

Commonly, livestock are identified on the farm through the use of identification tags, such as radio frequency identification (RFID) tags. According to various embodiments of the invention, the gait analysis apparatus 100 uses an identification antenna 102 matched to the identification tags in use on the farm to start the recording of measurements generated by a traversing test subject and to accurately identify the collected data to the test subject for proper diagnosis. Other similar automated identification means implemented in other settings (e.g., the healthcare and medical industries) are also contemplated to be part of this invention.

In a preferred aspect of the invention, impediments include an entry region 103 and an exit region 105, which are rigid platforms without sensing instrumentation. The entry region 103 and exit region 105 are configured to compel the animals to space themselves and walk through the system one at a time. A test subject may enter the gait analysis apparatus 100 via entry region 103, traverse through sensor region 104, and exit the system via exit region 105. By way of example and not limitation, the entry region 103 and exit region 105 may be ramps at a safe angle (e.g., <5°) to enter and exit the sensor region 104. By utilizing a ramp for the entry region 103, the test subject may easily reach the height (e.g., 1-5 inches or 3.75 inches in some embodiments) of the sensor region 104 in order to traverse the sensor region at a level and normal gait. Correspondingly, the use of a ramp for the exit region 105 allows the test subject safely exit the sensor region without interrupting its normal gait through the sensor region 104.

In another exemplary embodiment, the entry region 103 and exit region 105 may have the same height (e.g., 1-5 inches or 3.75 inches in some embodiments) as the sensor region 104, allowing for a normal gait while recording the acceleration and/or forces of a traversing subject on the sensor region 104. In this exemplary embodiment, the entry region 103 would consist of a step up for the test subject to enter the gait analysis apparatus 100 such that the test subject level its normal gait on the entry region 103 before traversing the sensor region 104. Further, the exit region 105 may have a step down to permit the test subject to exit the gait analysis apparatus 100 such that the test subject retains its normal level gait throughout its traversing of the sensor region 104. Without the rigid entry and exit regions 103, 105, normal gait would be unavailable. Rather, the test subject's climbing up to or stepping down from the platform would be measured. These dimensions may be freely varied in accordance with the size of the test subject to accomplish the intended result. For example, the length of the entry region 103 and exit region 105 may be sufficient to hold one full length of the test subject such that the test subject is at level gait prior to entering or exiting the sensor region 104.

While a step up/down entry and exit layout is illustrated herein, any combination of step up/down and ramps for the entry region 103 and exit region 105 may be suitable for the gait analysis apparatus 100 depending on the environment and test subjects. Further, as implemented for rodent applications and disclosed in U.S. Pat. No. 9,636,046, entitled "Diagnosis System and Method," and which is fully and expressly incorporated herein by reference, the entry region 103, sensor region 104 and exit region 105 may be at the same level without the need for step up/downs or ramps.

In one embodiment, the gait analysis apparatus 100 may include a sensor region 104 that measures one or more forces or accelerations imposed by a traversing test subject. The sensor region 104 may include at least one sensor module that includes load sensor modules 301, 302, 303 and/or acceleration sensor modules 304, 305, 306 as detailed further below. For example, the sensor module may consist of a single multidimensional load sensor and/or a single multidimensional accelerometer, and/or otherwise be coupled to a plurality of single-axis load sensors and/or single-axis or multidimensional accelerometers that are each configured to provide measurements of forces or accelerations imposed upon the sensor region 104 in one or more directions as the test subject traverses the apparatus. In particular, a sensor module may indicate a vertical force or acceleration imposed upon a load sensor or an accelerometer, a lateral load or acceleration imposed upon a load sensor or an accelerometer, and/or a for-aft load or acceleration imposed upon a load sensor or an accelerometer. In this manner, the gait analysis apparatus 100 may provide measurements of the various multidimensional loads and accelerations imposed upon the sensor region 104 as the test subject is traversing it to a gait measuring processing device 106. Exemplary embodiments of the sensor module are described in greater detail below with respect to FIGS. 3-9.

In particular, for four-legged test subjects, two or more floor plates 307 (see e.g., FIG. 3) of the sensor region 104 offsets the discrepancies caused by the inability to control the traversing speed of four-legged test subjects. For example, the sensor region may include two or more floor plates 307 that are positioned adjacently to one another. In a particular embodiment, the two or more floor plates 307 may be separated by a gap (e.g., 0.1 to 5 inches or 0.5 inches in some embodiments) to allow for each floor plate 307 to move independently of the other while maintaining a safe surface for the test subject to traverse the gait analysis apparatus 100. The dimension of the gap to separate the two or more floor plates 307 may be dependent on the size of the test subject.

Further, a single floor plate system (not illustrated) may be implemented for a sensor region 104 configured for a human or other bipedal animals traversing the gait analysis apparatus 100. In a preferred aspect such as for a bovine application, the sensor region 104 has a length of 50-100 inches or more preferred 72 inches and a top surface comprising anti-slip and corrosion-resistant flooring. Although the size and number of the plates may be varied in accordance with the invention, such variation may permit identification of the traversing test subject via the identification antenna 102 and measurement of the forces and accelerations for at least the hind limbs of four-legged animals in a single pass of the test subject through the gait analysis apparatus 100.

Each of the floor plates 307 may be constructed of a material that would encourage the test subject to traverse the sensor region 104. Thus, the floor plates 307 may be substantially rigid, such that a test subject feels secure traversing along the sensor region 104. The floor plates 307 may be made of a rigid material, such as plastic or metal, among other materials. Moreover, natural flexibility of the floor plates' 307 material should be minimized to reduce interference with the forces and accelerations generated by test subject on the sensor region 104.

The gait measuring processing device 106 may be communicably coupled via network 107 to sensor region 104 and output device 108 such that the load and acceleration measurements may be provided to the gait measuring processing device 106 for analysis and/or the output device 108 for display. For example, the network 107 may be a local area network (LAN) card to provide a data communication connection to a compatible LAN or via a direct connection, such as a USB connection, among others. Wireless links may also be implemented.

In a particular embodiment, the output device 108 may display the measurements of forces and accelerations, the diagnosis analysis and static weight measurements determined by the gait measuring processing device 106 to a user. For example, the output device 108 may display probabilities, scores, and/or simply a confirmation that the test subject does or does not suffer from a particular disease or dysfunction. In agriculture applications, the output device 108 may be incorporated into the farm's data management system, providing seamless incorporation of diagnostic tools into current infrastructure. For example, the output device 108 may be part of or incorporated into a general-purpose computer. By way of example and not limitation, gait measuring processing device 106 may identify the real-time costs and losses of lameness for dairy cattle (e.g., unrealized milk production, involuntary culling, and treatment expenses), daily weight measurements and extended weight monitoring of each individual cow in the herd. With an understanding of losses due lameness and weight monitoring in real-time, agriculture producers will be able to make better-informed decisions on how to manage the health of their herd and when to treat a suffering animal.

Figure 2:
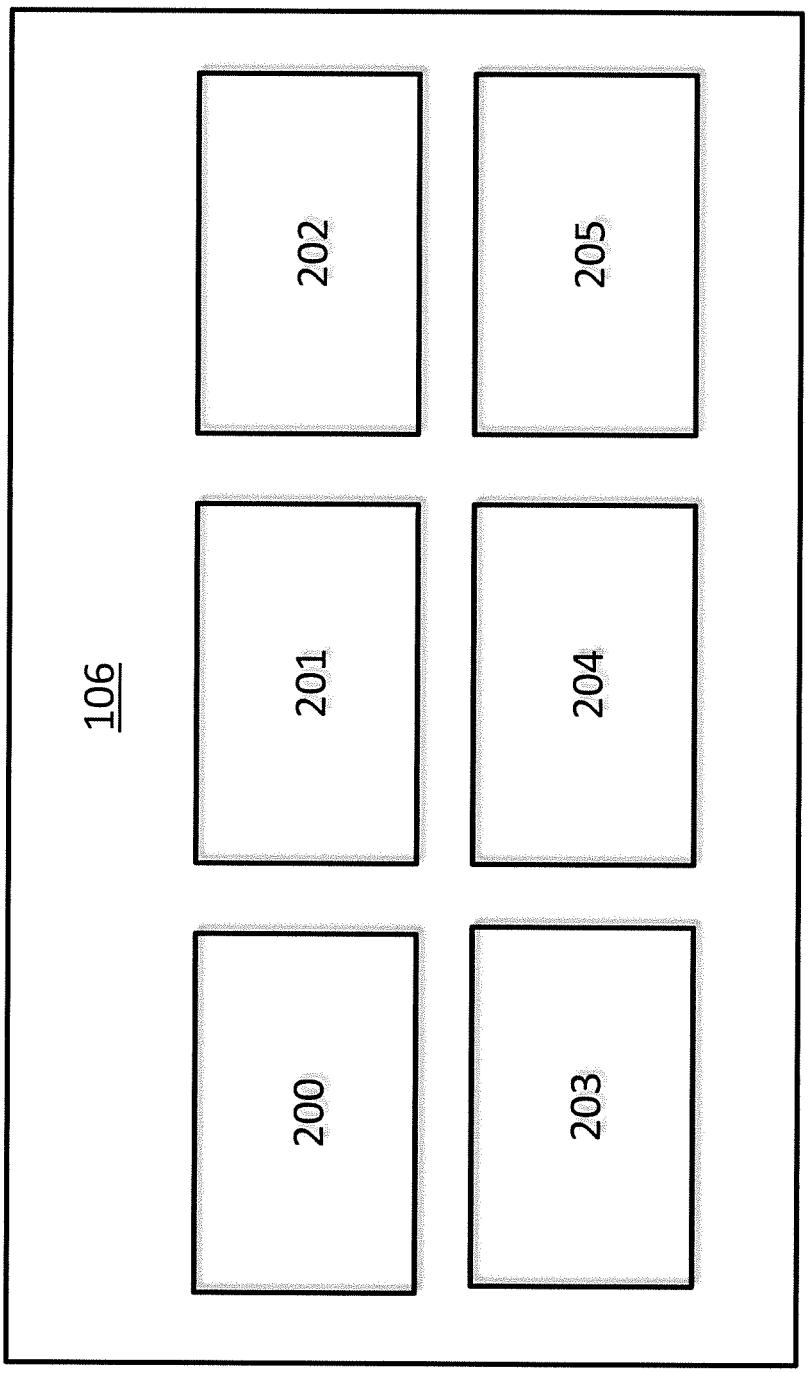
FIG. 2 is a block diagram of an exemplary gait measuring processing device according to an embodiment of the disclosure.

FIG. 2 is a block diagram of an exemplary gait measuring processing device 106 according to an embodiment of the disclosure. The gait measuring processing device 106 may include a receiver 200, a processor 201, a power supply 202, a storage device 203, low-pass filters 204 and data acquisition boards 205. Through various components, the gait measuring processing device 106 may receive and process various loads and/or accelerations placed upon the sensor region 104 as a test subject traverses the gait analysis apparatus 100. The processor 201 may be programmed to implement instruction to, for example, compare and analyze the measured loads and accelerations, among other things, diagnosing the test subject, monitoring measurements of the gait of the test subject over time, monitoring and determining of static weights and weight changes, and determining one or more biomarkers that indicate a diagnosis of a particular disease or dysfunction (e.g., lameness, ALS, and Parkinson's).

Based on the multidimensional measurements, the gait measuring processing device 106 may, for example, diagnose the test subject with a particular NM disease and/or injury or lameness, monitor progression of that ailment over time, and determine which measurements may be used as biomarkers to identify lameness or the particular NM disease and/or injury. By using measurements of loads and accelerations across multiple dimensions, stride length, and/or stance time, the apparatus may provide robust measurements of the gait of the test subject that may not only be used for diagnosis, monitoring, and identification of various dysfunctions, but it may also provide the static weight of the traversing test subject. For example, the gait measuring process device 106 may advantageously bolster the information available to dairy producer to make informed decisions to better manage the health of their herds.

According to various embodiments of the disclosure, the gait measuring processing device 106 may receive the multidimensional measurements of loads and accelerations from the gait analysis apparatus 100 described herein or other gait measurement apparatus. Based on the multidimensional measurements, the gait measuring processing device 106 may generate locomotion parameters (LPs) that each indicates empirical observation of a particular aspect of the gait of the test subject.

In a preferred embodiment of the invention, the gait measuring processing device 106 may perform statistical analyses on the LPs. For example, an analysis may include a statistical transformation, such as a non-optimal, optimal, identity, or spline. An identity transformation is a statistical analysis in which no mathematical transformation is executed. In a particular embodiment of the disclosure, a spline transformation may be utilized to analyze the LPs for a particular disease, such as, but not limited to, lameness, ALS, Parkinson, and muscular injury, and for an accurate static weight of the test subject as it traverses the gait analysis apparatus 100.

For example, to determine which LPs predict the diagnosis, LPs associated with test subjects known to be healthy with corresponding LPs of test subjects known to have a particular disease and/or injury ("unhealthy test subjects") may be compared. By way of example for applications to herd animals, the data from the sensor module is automatically generated into a log file along with the test subject's identification number, which is received by the receiver 200 from the identification antenna 102. The log files may be automatically saved when the next test subject in the herd enters the sensor region 104 or after a set period of time of recording (e.g., 3.5 seconds) had elapsed. The data from the sensor module (e.g., log files) may be saved to a storage device 203 for later retrieval and/or display to the output device 108 to a user.

According to various embodiments of the invention, data acquisition boards 205 may convert analog signals provided from the sensor module into a digital signal that may be utilized by the processor 201. In general, mechanical systems vibrate and/or move at relatively low frequencies (e.g., <100 Hz) and stray electro-magnetic interference (EMI) from electronics in the environment (e.g., system electronics, lighting, etc.) interfere with the signals being read by the data acquisition boards 205 at relatively high frequency. To remove high-frequency noise from the signals, low-pass filters 204 may be utilized to provide signals that accurately indicate the loads and accelerations measured by the sensor module.

As disclosed in U.S. Pat. No. 9,636,046, each LP (transformed or otherwise) may be analyzed to determine a misclassification rate for the LP. The misclassification rate may be generated by counting a number of unhealthy test subjects that have been incorrectly predicted to be healthy based on an analysis of each LP as compared to a number of unhealthy test subjects that have been correctly predicted to be unhealthy based on an analysis of each LP. For example, a control test subject (i.e., a healthy test subject) is tested a number of times to generate a model of the appropriate measurements of the LPs. After completion of a substantial sample, the generated model is applied to an unhealthy test subject (i.e., one suffering from lameness or induced with a NM dysfunction), who is tested a number of times. In consideration of the model generated by the control test subject, the probability that the unhealthy test subject belongs to the healthy (i.e., control) group or to a different group may be determined.

According to various embodiments of this invention, one or more LPs may be selected to generate a model based on loads and/or accelerations for purposes of weighing a traversing test subject. The model could use linear regression, logistic regression, neural networks, or any other modeling method. In another preferred embodiment of this invention, the load and acceleration measurements could be correlated and analyzed utilizing basic Newtonian principles of physics to determine a static mass and weight for each traversing test subject. For example, the processors 201 may be implemented with instructions to receive the load and acceleration measurements, determine the mass of the test subject by dividing the load measurements by the acceleration measurements, and then determine the weight of the test subject by multiplying its determined mass by gravity. Accordingly, the static weight of a test subject may be calculated for traversing test subjects without requiring the test subject to interrupt or halt its normal walking gait. This static weight monitoring advantageously allows farmers to accurately observe individual weights of a large herd of animals without requiring each animal of the herd to remain in a standstill position. Thus, the gait measuring processing device 106 may generate invaluable information for users, particularly for applications testing herds of animals, without any increased burden or cost.

Figure 3:
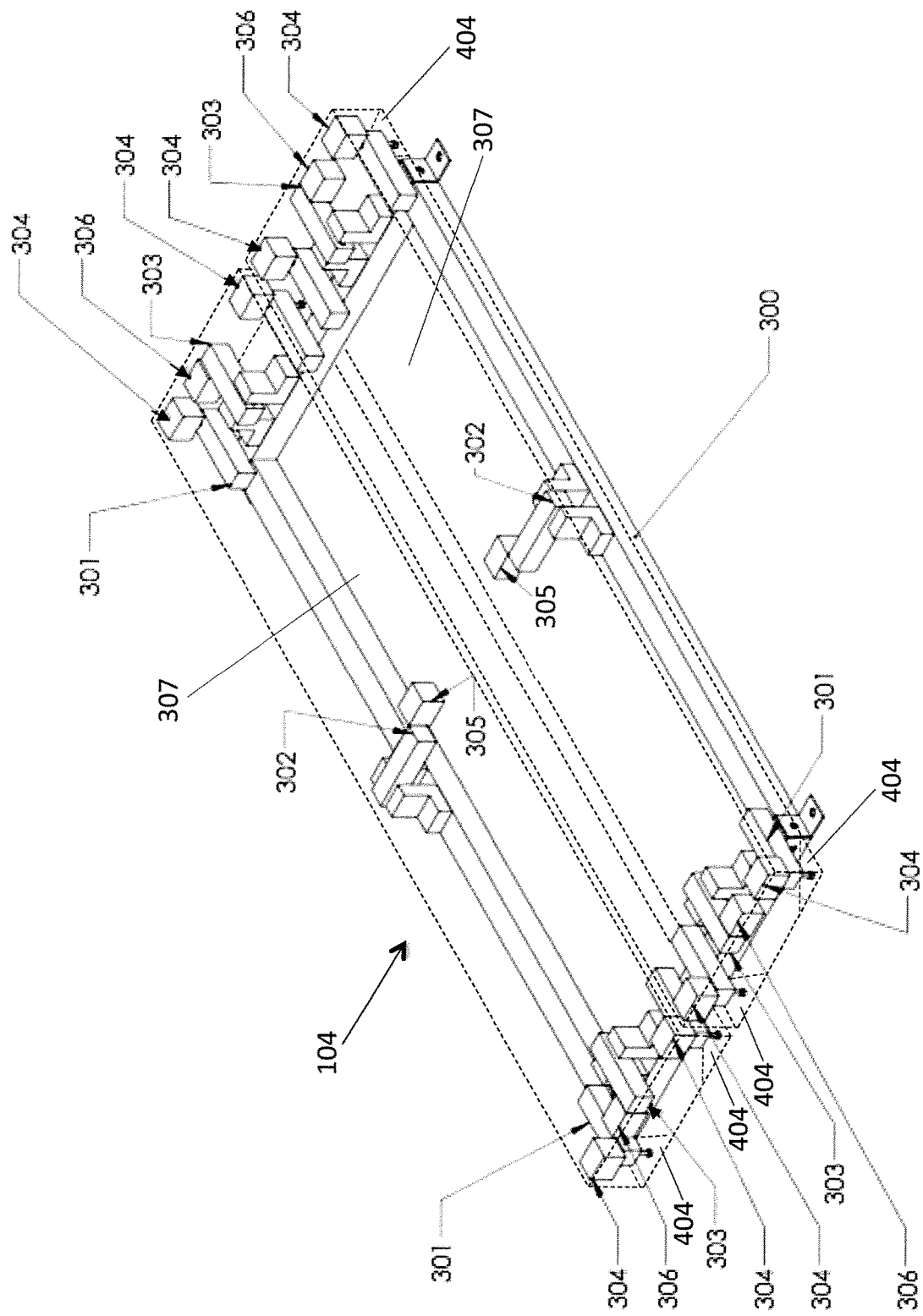
FIG. 3 is a schematic of one of the exemplary sensor region according to a first embodiment of the disclosure.

FIG. 3 is a schematic of one of the exemplary sensor region 104 according to a first embodiment of the disclosure. For purposes of explanation, the floor plates 307 are shown as dashed lines, illustrating the floor frame 300 and the configuration of the load and acceleration sensor modules 301, 302, 303, 304, 305, 306 beneath the floor plates 307 of the sensor region 104. As shown by way of example in FIG. 1, as test subject traverses gait analysis apparatus 100 from entry region 103 through sensor region 104 and exits the gait analysis apparatus 100 via exit region 105, sensor region 104 may be configured to measure forces and accelerations in multiple dimensions exerted on the floor plates 307 by a test subject.

For example, sensor region 104 may include or otherwise be coupled to at least one sensor module. A sensor module may incorporate at least one vertical load sensor module 301, at least one for-aft load sensor module 302, at least one lateral load sensor module 303, at least one vertical acceleration sensor module 304, at least one for-aft acceleration sensor module 305, and at least one lateral acceleration sensor module 306. In a preferred embodiment, the acceleration sensor modules 304, 305, 306 each include multidimensional accelerometer (wherein a single multidimensional acceleration sensor is capable of measuring vertical, for-aft, and lateral accelerations) and/or each single-axis accelerometers providing measures for their respective directions. For example, the load sensor modules 301, 302, 303 may also be a multidimensional load sensor (not shown; wherein a single multidimensional load sensor is capable of measuring vertical, for-aft, and lateral forces) and/or each may be a single-axis load sensor measuring loads in each of their respective directions.

Vertical load sensor module 301, for-aft load sensor module 302, lateral load sensor module 303, vertical acceleration sensor module 304, for-aft acceleration sensor module 305, and lateral acceleration sensor module 306 may provide one or more measurements of vertical (or up-down), for-aft (or front-back), and lateral (or side-to-side) loads and accelerations, respectively. In a hypothetical X-Y-Z coordinate system (not shown) where the test subject traverses sensor region 104 along substantially the Y-axis (horizontally), vertical load sensor module 301 may measure vertical (up-down along the Z-axis) forces, vertical acceleration sensor module 304 may measure vertical (up-down along the Z-axis) accelerations, for-aft load sensor module 302 may measure for-aft (front-back along the Y-axis) forces in directions pointing to and from entry region 103 and exit region 105, for-aft acceleration sensor module 305 may measure for-aft (front-back along the Y-axis) accelerations in directions pointing to and from entry region 103 and exit region 105, lateral load sensor module 303 may measure lateral (side-to-side along the X-axis) forces, and lateral acceleration sensor module 306 may measure lateral (side-to-side along the X-axis) accelerations. In this manner, using sensor modules 301, 302, 303, 304, 305, 306 to measure multidimensional loads and accelerations, the sensor region 104 may provide measurements imposed upon the gait analysis apparatus 100 as a test subject is traversing it to generate robust data for analysis of the test subject's gait.

As described in more detail below with respect to FIGS. 4-6, the load sensor modules 301, 302, 303 may be altered to replace each of the load sensors 403, 503, 603 with restriction block 405 in order to provide an exemplary embodiment of the invention that solely measures accelerations via the acceleration sensor modules 304, 305, 306. Among other benefits, by removing the need for load sensors 403, 503, 603, the overall cost for manufacturing and maintenance of the gait analysis apparatus 100 may be greatly reduced without eliminating the benefits of the novel suspension design described in greater detail herein. For example, at least four multidimensional accelerometers sealed from outside hazards are installed on each of the floor plates 307 in each corner at both sides adjacent to the entry region 103 and exit region 105. The measurements from the multidimensional accelerometers are correlated to the floor vibrations that are induced by the test subjects. By utilizing only the floor vibrations measured by the accelerometers, the gait analysis apparatus 100 may distinguish between healthy and unhealthy test subjects (e.g., sound and lame cows) for purposes of diagnostics and monitoring of lameness and/or NM diseases or dysfunctions. Thus, the overall system design can be simplified significantly, reducing the manufacturing cost of the system and other benefits. Accelerometers are also much more reliable with respect to accurate measurements in harsh environments such as dairy farms and thus drastically reducing the maintenance costs or burdens of the system.

In a particular embodiment, a test subject enters the gait analysis apparatus 100 via entry region 103, walks across the sensor region 104 at level normal gait, and then exits the gait analysis apparatus 100 via exit region 105. Each of the floor plates 307 of the sensor region 104 may move independently of one another. As such, each floor plate 307 may be associated with or be coupled to respective sensor modules for both loads and accelerations. For example, each floor plate may be coupled to: four vertical load sensor modules 301, one for-aft load sensor module 302, two lateral load sensor modules 303, four vertical acceleration sensor modules 304, one for-aft acceleration sensor modules 305, and two lateral acceleration sensor modules 306. In this manner, the floor plates 307 may be coupled to a total of fourteen load sensors and fourteen accelerometers, which each may be single-axis or multidimensional sensors. Thus, as the test subject traverses the sensor region 104, force and acceleration measurements may be provided across multiple dimensions. In an exemplary embodiment of the invention, a gait analysis apparatus 100 may consist of four acceleration sensor modules each containing a multidimensional accelerometer to measure accelerations in all three directions. In this exemplary embodiment, each of the four acceleration sensor modules may be attached to each floor plate 307 at the four outer corners of the sensor region 104 as depicted by way of example by the vertical acceleration sensor module 304.

Figure 4:
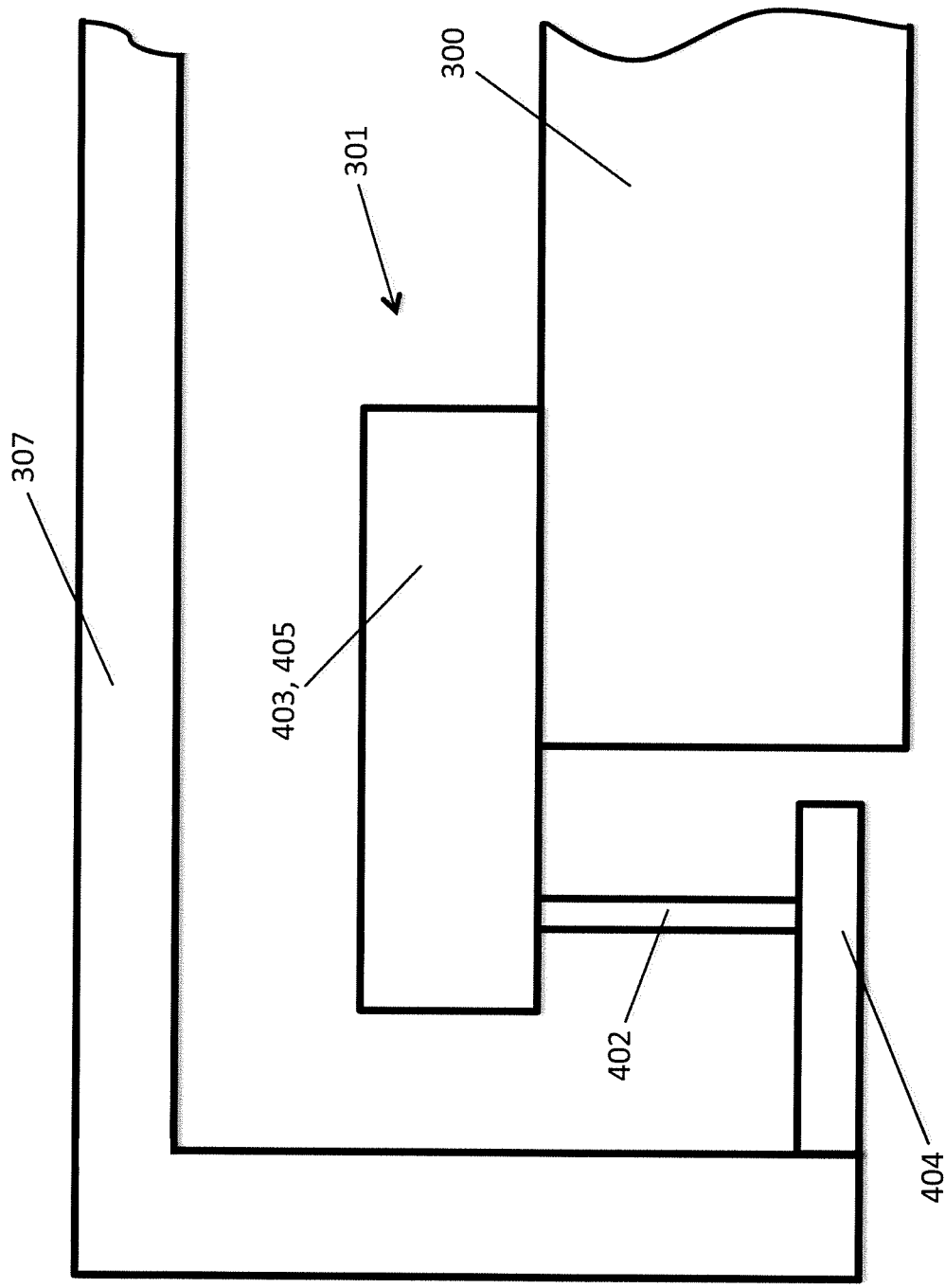
FIG. 4 is an elevation view of an example of one of the vertical load sensor module according to an embodiment of the disclosure.

FIG. 4 is an elevation view of an example of one of the vertical load sensor module 301 that includes a vertical load sensor 403 according to an embodiment of the disclosure. According to various embodiments of the disclosure, floor frame 300 of the sensor region 104 may be coupled to vertical load sensor 403. A flexible link 402 may be coupled to the vertical load sensor 403 such that the flexible link 402 hangs from the vertical load sensor 403, suspending the sensor region 104 from the vertical load sensor module 301.

The flexible link 402 may be, for example, a string, wire, rope, cable, chain, etc. The flexible link 402 may be composed of a material such as, for example, nylon, metal, natural fibers, or any other flexible material. The required degree of flexibility and strength for flexible link 402 depends on the size of the test subject and the magnitude of forces and/or accelerations being applied to the floor plates 307 by the test subject. Thus, for a test subject with a considerable mass, such as a horse or cow, a stronger flexible link, such as a chain, may be necessary. In comparison, for test subjects of lesser proportions, such as rodents, a nylon string may be sufficient.

Flexible link 402 may be coupled to a suspension plate 404, which may be a part of each of the floor plates 307 of the sensor region 104. As also shown in FIG. 3, a suspension plate 404 may be formed at the outer four corners of each the sensor region 104 on the bottom of the floor plates 307. Thus, according to the embodiment illustrated in FIG. 4, the flexible link 402 may provide a suspended sensor region 104 such that the floor plates 307 are suspended from the vertical load sensor module 301 in the vertical direction via floor frame 300 and the vertical load sensors 405. Thus, a vertical load applied to the sensor region 104, such as when test subject steps onto or off sensor region 104, may cause suspension plate 404 to move in a vertical direction, causing flexible link 402 to exert a vertical load, and causing vertical load sensor 403 to measure the applied vertical load.

Among other advantages, by configuring a suspended sensor region 104, any interference in the forces and/or accelerations due to friction become negligible in all directions. Accordingly, by suspending the sensor region 104 from the vertical load sensor module 301, the sensor region 104 is free to move in all directions for accurate force and acceleration data collection as detailed further below. While suspension of the sensor region 104 is only illustrated in this exemplary embodiment in the vertical direction, the gait analysis apparatus 100 may be configured to be suspended in any of the directions (i.e., vertical, for-aft, or lateral) such that the friction forces would be eliminated in the for-aft and lateral directions as well.

According to various embodiments of the invention, each of the vertical load sensors 403 of the vertical load sensor modules 301 may be removed from the gait analysis apparatus 100 and replaced with a restriction block 405 of the same size and shape of the vertical load sensors 403. For example, the restriction block 405 may be made of metal or plastic depending on the forces and accelerations to be applied to the gait analysis apparatus 100. The restriction block 405 may be configured to provide the same structural functions and benefits of suspension to the gait analysis apparatus 100 but does not provide a vertical load measurement. Rather, the gait analysis apparatus 100 may be configured to operate solely on the acceleration sensor modules 304, 305, 306. One of many advantages to such a system is that accelerometers may be more suitable for agriculture environments, because accelerometers are not affected by changes in temperature like load sensors, which are susceptible to lose accuracy throughout the normal daily shifts in temperature (e.g., <10° change).

Figure 5:
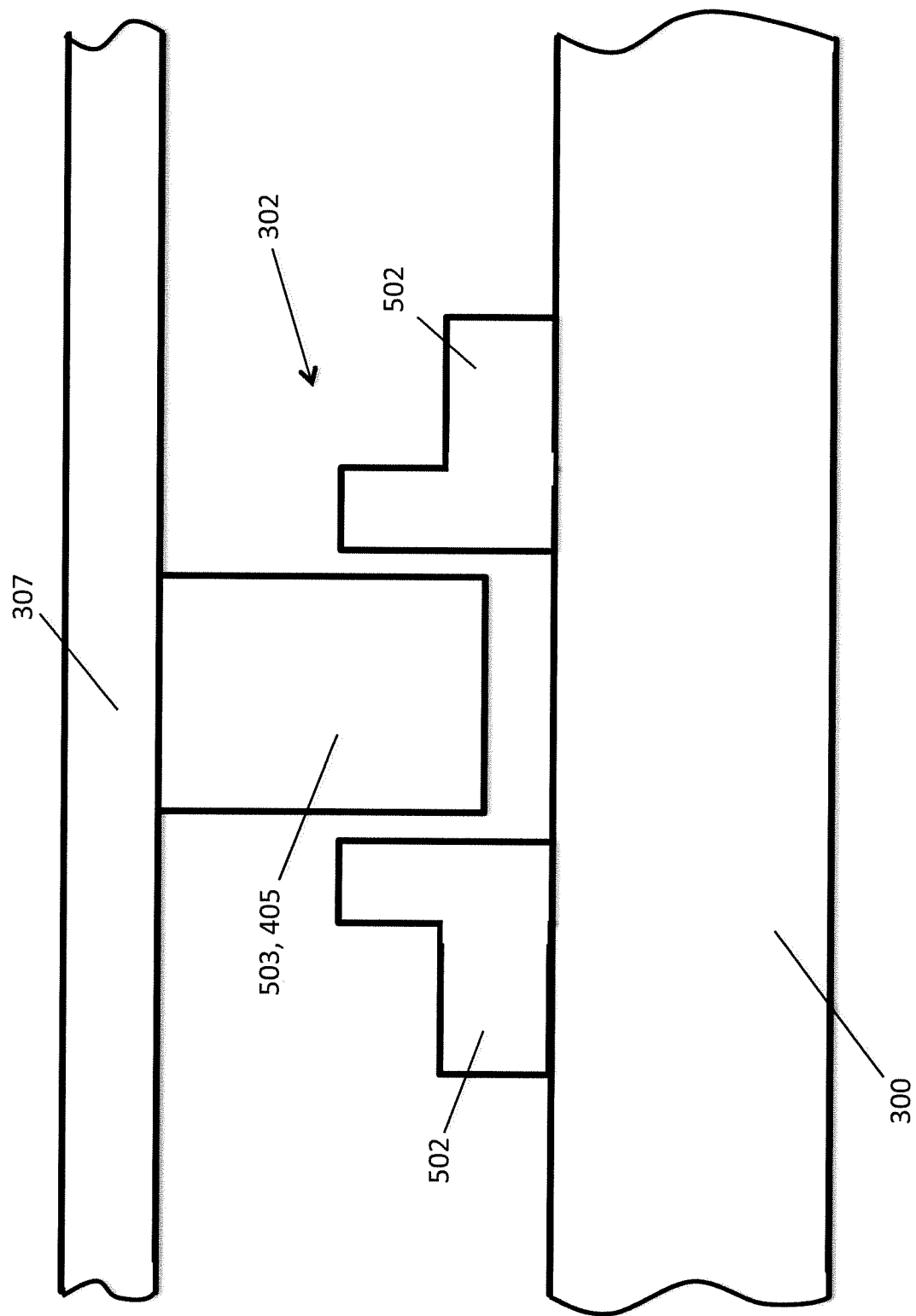
FIG. 5 is an elevation view of an example of one of the for-aft load sensor module according to an embodiment of the disclosure.

FIG. 5 is an elevation view of an example of for-aft load sensor modules 302 that includes a for-aft load sensor 503 according to an embodiment of the disclosure. According to various embodiments of the disclosure, a pair of limiting members 502 may be coupled to the floor frame 300 of the sensor region 104, such that the limiting members 502 are affixed to the floor frame 300 on opposite sides of the for-aft load sensor 503. The for-aft load sensor 504 may be coupled and affixed to each of the floor plates 307 of the sensor region 104.

The limiting members 502 may be configured to permit the sensor region 104 (i.e., each of the floor plates 307) to move a limited amount of distance (e.g., less than about 1 mm). In other words, the limiting members 502 may be arranged to limit the freedom of movement of the sensor region 104. The limited amount of distance that each of the floor plates 307 is permitted to move relative to the for-aft load sensor module 302 may depend on the size of the test subject such that a rigid surface is provided for the test subject to traverse the sensor region 104. The for-aft load sensor 503 may be coupled to sensor region 104 such that a for-aft load applied to sensor region 104 (such as when a test subject steps onto or off) may cause the for-aft load sensor 503 to move with each of the floor plates 307 of the sensor region 104 the limited amount of distance between the limiting members 502, causing for-aft load sensor 503 to measure the applied for-aft load. In this exemplary embodiment of the invention, the number of moving mechanical components for the suspension design of the gait analysis apparatus 100 may be minimized, reducing the likelihood of mechanical failure. Accordingly, such a design may be advantageous for smaller sized test subjects (e.g., rodents) where issues of overloading due to jumping or running by the test subject are not as significant as compared to larger sized test subjects (e.g., cows).

As discussed with reference the vertical load sensors 403 shown in FIG. 4, the for-aft load sensor 503 may be replaced with a restriction block 405, which lacks any measurement functionalities. The restriction block 405 acting in place of the for-aft load sensor 504 (as described above) may be configured to function with the limiting members 502 to permit each of the floor plates 307 of the sensor region 104 to move a limited amount of distance. In such a configuration, measurement of the applied forces would not be necessary for purposes of analysis and the gait analysis apparatus 100 would only measure accelerations imposed on the sensor region 104 as described further with respect to FIG. 7. Such a system may be advantageous because accelerometers are more durable than load sensors and accelerometers can withstand much larger forces, typically caused by unnatural walking behavior such as jumping, before becoming damaged in comparison to most conventional load sensors. Accordingly, utilization of restriction blocks 405 still provide the novel limited freedom of movement benefits of the suspension design detailed herein with respect to the negation of any friction effects to produce accurate gait measurement for analysis without the added cost of load sensors.

Figure 6:
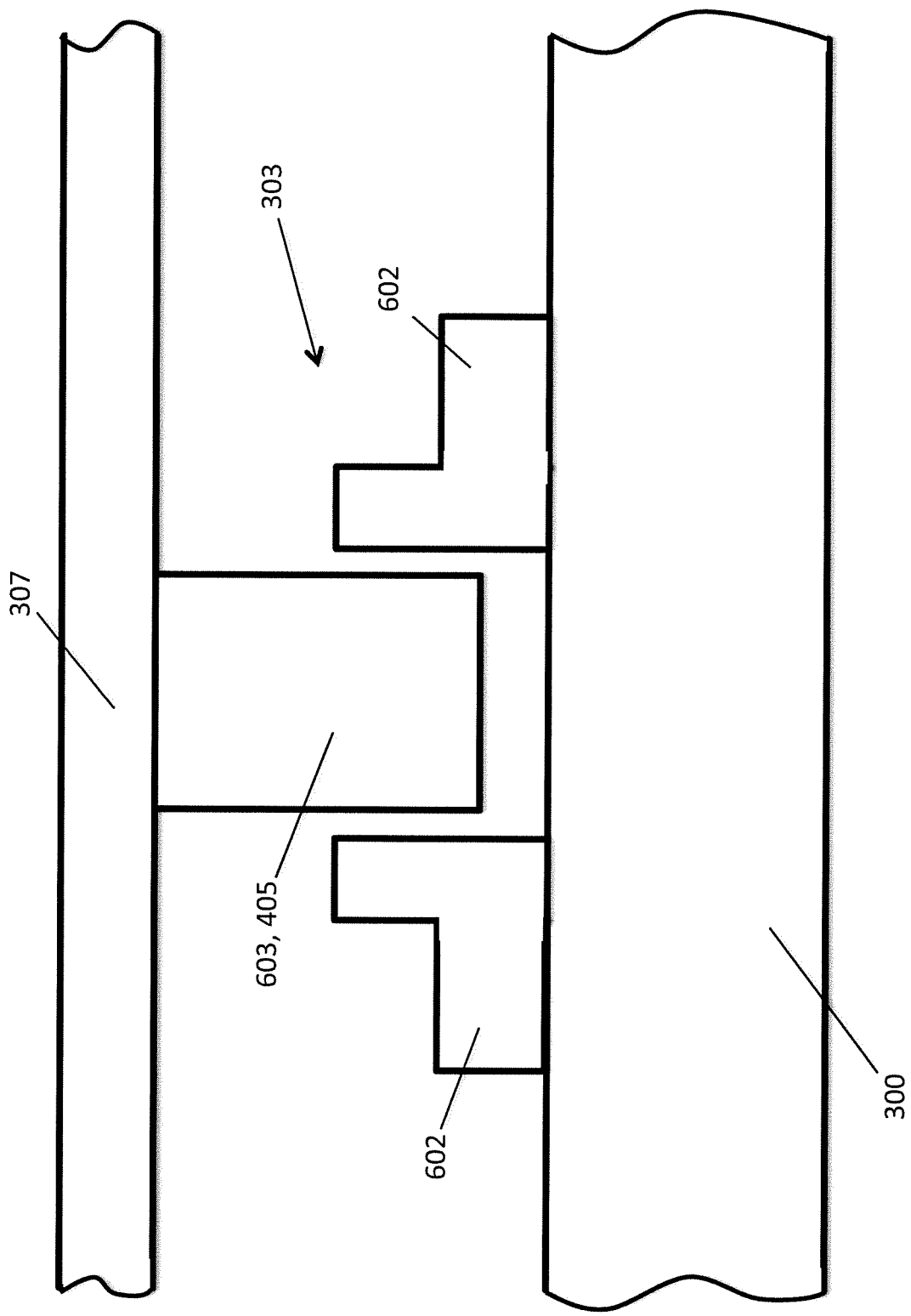
FIG. 6 is an elevation view of an example of one of the lateral load sensor modules according to an embodiment of the disclosure.

FIG. 6 is an elevation view of an example of the lateral load sensor modules 303 that includes a lateral load sensor 603 according to an embodiment of the disclosure. According to various embodiments of the invention, the floor frame 300 of the sensor region 104 may be coupled to a pair of limiting members 602, such that the limiting members 602 are affixed to the floor frame 300 on opposite sides of the lateral load sensor 603. Lateral load sensor 603 may be coupled to the sensor region 104 (i.e., each of the floor plates 307), such that lateral load sensor 603 is affixed to and moving with the floor plates 307 of the sensor region 104.

The limiting members 602 are configured to permit the sensor region 104 (i.e., each of the floor plates) to move a limited amount of distance (e.g., less than about 1 mm) relative to the lateral load sensor module 303 so long as the test subject is provided a rigid and secure surface to traverse. In other words, the limiting members 602 are arranged to limit the freedom of movement of each of the floor plates 307 of the sensor region 104. The lateral load sensor 603 may be coupled to each of the floor plates 307 of the sensor region 104 such that a for-aft load applied to sensor region 104 (such as when a test subject steps onto or off) may cause the lateral load sensor 603 to move with the floor plates 307 of the sensor region 104 the limited amount of distance between the limiting members 602, causing the lateral load sensor 603 to measure the load applied in the lateral direction. In addition to the benefits described above in FIG. 5, the gouging or boring of the lateral load sensors 603 that may be caused by the limiting members 602 is also diminished. Thus, by coupling the limiting members 602 to the floor frame 300 of the sensor region 104 and the lateral load sensors 603 to the bottom of the floor plates 307 of the sensor region 104, the chances of mechanical failure of the lateral load sensor modules 303 is decreased. These improvements, among other benefits, also prevent deterioration of the gait analysis apparatus 100 with time in operation in harsh environments such as commercial dairy farms.

As discussed with reference to FIGS. 4 and 5, the lateral load sensor 603 may be replaced with a restriction block 405, which functions structurally as the lateral load sensor 603 but does not provide any measurement capabilities. The restriction block 405 acting in place of the lateral load sensor 603 (as described above) may be configured to function with the limiting members 602 permitting each of the floor plates 307 of the sensor region 104 to move a limited amount of distance between the limiting members 602 (e.g., less than about 1 mm). The movement of the limited amount of distance by the sensor region 104 causes the lateral load sensor module 303 to measure the loads in the lateral direction. By eliminating the force measurement capabilities, the gait analysis apparatus 100 would simply measure accelerations imposed on the sensor region 104 and provide a number of advantages over merely a force measurement system as detailed below.

Figure 7:
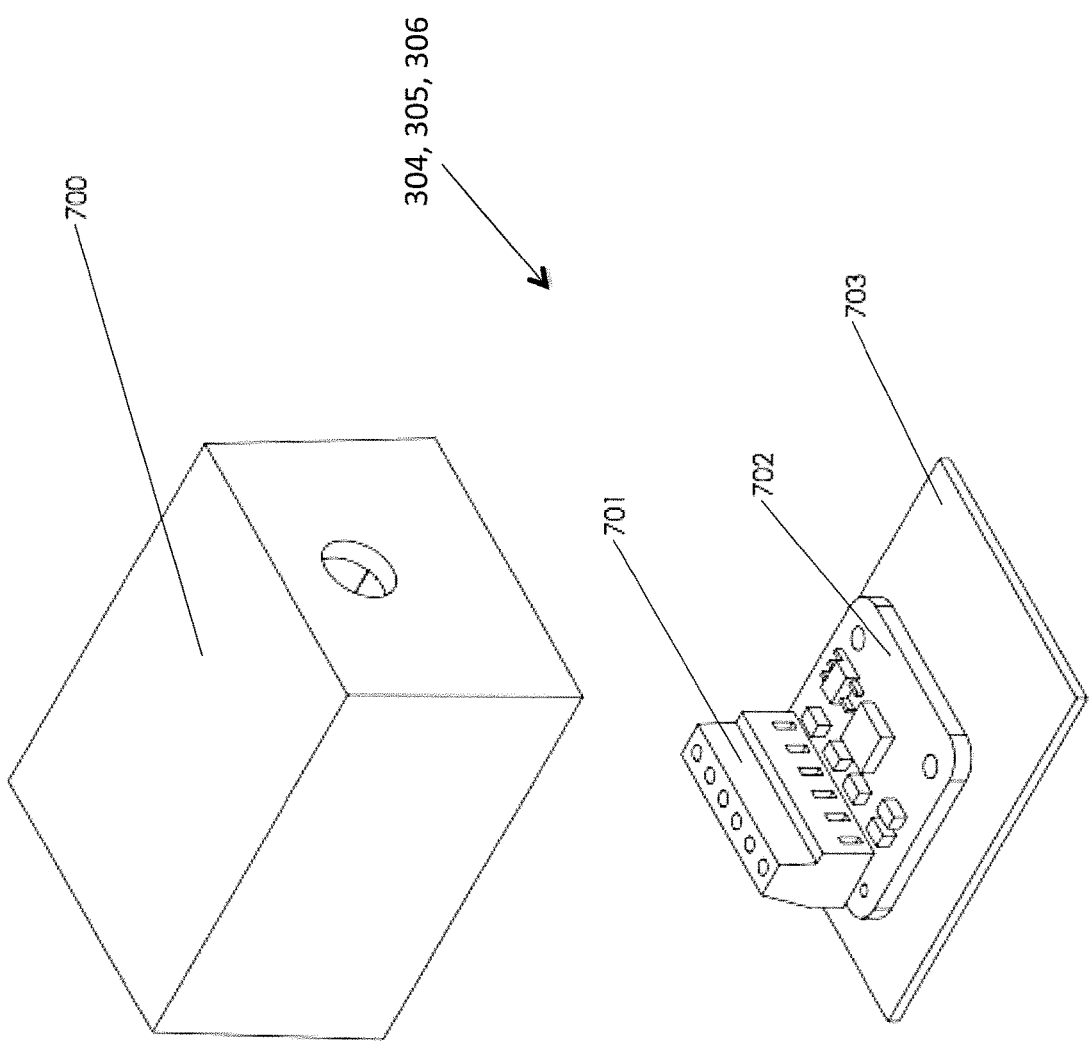
FIG. 7 is an illustration of one example of the acceleration sensor modules according to an embodiment of the disclosure.

FIG. 7 is an illustration of one example of acceleration sensor modules 304, 305, 306 according to an embodiment of the disclosure. Acceleration sensor modules 304, 305, 306 may include a cover 700, an input/output terminal 701, an accelerometer 702, and a base 703. For purposes of illustration, the cover 700 is removed from the base 703 to reveal the internal components of the acceleration sensor modules 304, 305, 306. As the gait analysis apparatus 100 is traversed by the test subject, the acceleration sensor modules 304, 305, 306 may measure, among many other variables, the accelerations related to a walking gait of the test subject resulting from the traversal in multiple dimensions. Each of the acceleration sensor modules 304, 305, 306 may be affixed to the sensor region 104 by being attached to the bottom of the top surface of each of the floor plates 307 of the sensor region 104.

According to various embodiments of the invention, the accelerometer 702 includes an accelerometer capable of measuring accelerations in a single and/or multiple dimensions (i.e., vertical, for-aft, and/or lateral). The accelerometer 702 is mounted to a printed circuit board that includes an on-board low pass filter. Thus, advantageously reducing the number of operations and elements needed in the gait measuring processing device 106 for the analysis of the accelerations. An adhesive may be used to hold the accelerometer 702 securely to base 703. For example, the adhesive may be a strip of double-sided foam tape.

The input/out terminal 701 is structurally and electronically coupled to the circuit board, providing a means to output the measured accelerations to, for example, the gait measuring processing device 106. An opening is provided in the cover 700 to permit a wire that connects the accelerometer 702 via the input/output terminal 701 to, for example, the gait measuring processing device 106. It may also be possible to use other means of communication, including, but not limited to, wireless connection such that the cover 700 would not need an opening. The cover 700 and base 703 are configured to be coupled together in order to enclose the accelerometer 702 and input/output terminal 701, protecting the internal components from outside hazards. In particular, for agriculture applications, the cover 700 and base 703 advantageously protect the internal components from outside environmental hazards such as water damage, among other potentially damaging environmental vulnerabilities. Further, the acceleration sensor modules 304, 305, 306 may be insulated after installation onto the gait analysis apparatus 100. For example, an electrical insulating varnish may be sprayed on to fill any gaps and create an abrasion-resistant and wear-resistant coating to insulate the acceleration sensor modules 304, 305, 306 and protect the internal components, which will further facilitate application of the invention in harsh environments such as farms.

In a preferred embodiment of the invention, the vertical load sensors 603, for-aft load sensors 403, and lateral load sensors 503 may be removed and replaced with restriction blocks 405 that act to provide the same structural functionality with respect to the suspension and movement of the sensor region 104 as detailed herein. The restriction blocks 405 may be the same shape and size of the load sensors 403, 503, 603 to permit each of the floor plates 307 of the sensor region 104 to move the limited amount of distance as described with respect to FIGS. 4-6, but the restriction blocks 405 do not provide any sensing and/or measuring capabilities. By removing the load sensors 403, 503, 603 from the gait analysis apparatus 100 and installing restriction blocks 405 in their place, only the accelerations of a traversing test subject would be measured and provided to the gait measuring processing device 106 to process, analyze and/or display, among other functions, as described above with respect to FIGS. 1-3.

There are a number of advantages to a gait analysis apparatus 100 that includes only acceleration sensor modules 304, 305, 306 and eliminates the need for any load sensors 403, 503, 603. For example, load sensors are readily affected by changes of temperature, even minimal changes of less than ten degrees, while accelerometers are stable across a daily temperature range. As temperature changes, the voltage output from the load sensors drifts leading to inaccuracies in measurements. These issues must be corrected manually by taring the system (i.e., zeroing the system) to correct for the error caused by temperature drift. Because load sensor temperature-dependent drift is susceptible to minimal variance, such as a less than 10° change, this problem can become a hindrance for operation of the system in a non-temperature controlled environment such as farms.

By way of further example, load sensors are more difficult to maintain than accelerometers. When load sensors are overloaded (e.g., caused by running/jumping by a test subject) their internal electronics become damaged and they must be replaced. Accelerometers are more durable and can withstand much larger measurements before becoming damaged. Even in a situation where acceleration sensor modules 304, 305, 306 do become damaged and require replacement, the process is much simpler and less extensive than replacing load sensors 403, 503, 604. Unlike the load sensors 403, 503, 603, the acceleration sensor modules 304, 305, 306 are not structural parts of the gait analysis apparatus 100. In other words, the load sensors 403, 503, 603 themselves are configured to function with other elements of the gait analysis apparatus 100 to limit movement of the sensor region 104 relative to a load sensor module such that replacing a load sensor requires disassembling structural portions of the sensor region 104. In contrast, acceleration sensor modules 304, 305, 306 may be simply affixed to the bottom of the floor plates 307 of the sensor region 104. In a preferred embodiment, an access door may be provided in the floor plates 307 to allow easy and simple maintenance and replacement of the acceleration sensor modules 304, 305, 306.

Accordingly, the reduced need for maintenance and a simpler maintenance protocol may result in a gait analysis apparatus 100 that replaces the load sensors 403, 503, 603 with restriction blocks 405 as described in greater detail above. On average, load sensors cost much more than accelerometers. For example, the price of a multidimensional accelerometer is $200, compared to $650 for one single-axis load sensor and $25,000 for a multidimensional load sensor. This cost savings will result in a significantly lower manufacturing cost for the gait analysis apparatus 100.

In sum, a gait analysis apparatus 100 comprised of both sensors to measure both accelerations and forces, respectively, may provide robust measurements that may be analyzed for, among other things, weighing the test subject, diagnosing the test subject, monitoring measurements of the gait of the test subject over time, and determining one or more biomarkers that indicate a diagnosis of a particular disease or dysfunction (e.g., lameness, ALS, and Parkinson's). Further, a gait analysis apparatus 100 comprised solely of sensors to measure accelerations may provide the same analytical functionality but at a cost that is significantly reduced, among other benefits.

FIGS. 8(a) and 8(b) are illustrations of another example of acceleration sensor modules 304, 305, 306 according to an embodiment of the disclosed invention. Please note that all of the functionalities described above in FIG. 7, particularly in regards to measuring multiple dimensions, are applicable to the exemplary acceleration sensor modules 304, 305, 306 shown in FIGS. 8(a) and 8(b). FIG. 8(a) shows exemplary acceleration sensor modules 304, 305, 306 without a top cover 801, revealing the internal components of the acceleration sensor module. And, FIG. 8(b) depicts these exemplary acceleration sensor modules 304, 305, 306 closed with a top cover 801, which is preferably its operational configuration.

As shown in FIG. 8(a), molded clips 805, holding the accelerometer 702 safely against the bottom cover 802, secure the accelerometer 702 in place, which may be a single-axis accelerometer or multidimensional accelerometer. Further as discussed above in regards to FIG. 7, the accelerometer 702 comprises of an input/output terminal, providing a means to output the measured accelerations to, for example, the gait measuring processing device 106. A cut-out is provided between the top cover 801 and bottom cover 802 when in its closed position in order to hold a gasket 803, preferably made of rubber, having a void 804 to allow an electrical wire to pass through the cover 801, 802 and establish an electrical connection between the accelerometer 702 and the gait measuring processing device 106. The gasket 803 ensures a tight seal between the top and bottom covers 801, 802, protecting the accelerometer 702 from outside environmental hazards such as water damage. Each of the acceleration sensor modules 304, 305, 306 may be affixed to the sensor region 104 by screwing the bottom cover 802 to the bottom of the top surface of each of the floor plates 301 via each of the mounting assemblies 806 (e.g., utilizing a square nut). To further protect the accelerometer 702 from the environment or outside dangers, the closed housing depicted in FIG. 8(b) may be filled with an epoxy or resin or electrical insulating varnish may be sprayed on to fill any gaps and create an abrasion-resistant and wear-resistant coating to insulate the acceleration sensor modules 304, 305, 306 and guarantee a watertight seal of the internal components.

FIG. 9 provides another exemplary embodiment of the invention. In this second embodiment, the sensor region 104 may consist of all the features described in the previous embodiment described in detail above. In particular, the floor plates 307 may be comprised of acceleration sensor modules 304, 305, 306 (not shown in FIG. 9), a for-aft load sensor modules 902, a lateral load sensor modules 903, and a vertical load sensor modules 301. However, unlike the previous embodiment detailed above, the for-aft load sensor modules 902 and lateral load sensor modules 903 are configured to suspend the floor plates 307 from the floor frame 300 in each of their respective directions. As detailed further below, the limiting members 502, 602 include a suspension assembly 910, 912 to suspend the sensor region 104 from their respective load sensor modules 902, 903 in their respective directions. Accordingly, the sensor region 104 may be suspended in numerous directions and locations in the structure, and not simply in the vertical direction from each of the vertical load sensor modules 301. Thus, reducing the likelihood of suspension failure and increasing the system's performance and durability. Please note that all of the limitations and advantages detailed above with respect to the first exemplary embodiment of the invention are applicable to the second embodiment described herein.

FIG. 10 depicts the bottom view of the sensor region 104 according to the second exemplary embodiment of the invention. As detailed above in FIGS. 3 & 4, the vertical load sensor modules 301 shown here are also comprised of, among other features, a suspension plate 404 and a flexible link 402. Thus, a vertical load applied to the sensor region 104, such as when test subject steps onto or off sensor region 104, may cause suspension plate 404 to move in a vertical direction, causing flexible link 402 to exert a vertical load, and thus vertical load sensor modules 301 may measure the applied vertical load. In contrast to the first embodiment, each one of the for-aft load sensor modules 902 and lateral load sensor modules 903 comprised of a load sensor 503, 603 which is coupled to and affixed to the floor frame 300, such that each of the load sensors 503, 603 remain stationary during operation of the gait analysis apparatus 100. Further in contrast, each of the limiting members 502, 602 of the for-aft load sensor modules 902 and lateral load sensor modules 903 includes a suspension assembly 910, 912, which is coupled to each of the floor plates 307 of the sensor region 104. In such an exemplary embodiment, the limiting members 502, 602 of the for-aft load sensor modules 902 and lateral load sensor modules 903 via their respective suspension assemblies 910, 912 are coupled to the sensor region 104 and configured to move with the sensor region 104 to limit movement of the sensor region 104 a limited amount of distance relative to its respective load sensor module 902, 903. Movement of the limiting members 502, 602 via their respective suspension assemblies 910, 912 causes the for-aft load sensor modules 902 to measure the loads in the for-aft direction and the lateral load sensor modules 903 to measures the loads in the lateral direction. Accordingly, the suspension assembly 910, 912 is configured to allow measurement of an applied load on the sensor region 104 in each of the respective directions (i.e., for-aft and lateral) of the load sensor modules 901, 902 by the for-aft load sensors 503 and the lateral load sensors 603.

Each of the for-aft load sensors 503 and lateral load sensors 504 are coupled to the floor frame 300 and a suspension assembly 910, 912. In this exemplary embodiment, the stationary for-aft load sensors 503 and lateral load sensors 504 are attached to the suspension assembly 910, 912 via a coupling screw 932, but any means capable of securing attaching the fixed load sensors 503, 504 to the moveable suspended holder 930 of the suspension assembly 910, 912 would suffice. This particular configuration illustrated here of coupling the for-aft and lateral sensor modules 901, 902 by suspending them from the floor plates 307 provides numerous benefits. For example, in particularly harsh environments, such as the operation of the gait analysis apparatus 100 on a commercial farm for purposes of lameness diagnosis, the gait analysis apparatus 100 must withstand heavy loads (e.g., a dairy cow's average weight is between 1,500-2,000 lbs) on a continuous basis (e.g., daily). To ensure durable and accurate results over a long product-life cycle (minimum 1 year), the suspension assembly 910, 912 of the limiting member 502, 602 eliminate the possibility of the limiting members 502, 602 gouging or boring into the load sensors 503, 504 or any other part of the gait analysis apparatus 100. Gouging or boring of the analysis apparatus' 100 components may lead to loss of suspension, and thus its advantages for the system. Specifically, the configuration of the gait analysis apparatus 100 can become misaligned, which offloads the sensors resulting in, among many problems, inaccurate data and eventual total system failure. In light of the commercial farm setting and its requisites for durability, it is likely that the simpler design (e.g., fewer moving components) detailed with respect to the first exemplary embodiment above may be more advantageous, for example, the testing of rodents in a pharmaceutical research setting. Nonetheless, suspension of the sensor region 104 in all three directions reduces the issue of the limiting members 502, 602 gradually boring into the load cells 503, 504 and causing the gait analysis apparatus 100 to inaccurately measure the gait of the traversing test subject. Please note that this issue is mostly due to irregular strong forces exerted by the test subject (e.g., a cow jumping on the machine), but is, nonetheless, a durability issue needed to be addressed for certain applications (e.g., dairy producers).

As discussed above with reference to FIGS. 3-6, all of the load sensors 403, 503, 603 may be replaced with a restriction block 405, which lacks any measurement functionalities. The restriction block 405 acting in place of the load sensors 503, 603 may be configured to function with the suspension assembly 910, 912 as detailed herein to suspend the sensor region 104 from the lateral load sensor module 903 in the lateral direction and from the for-aft load sensor module 902 in for-aft direction. The restriction blocks 405 may be coupled to the sensor region 104 to move with and permit each of the floor plates 307 of the sensor region 104 to move a limited amount of distance relative to their respective load sensor modules 902, 903. In such a configuration, measurement of the applied forces would not be necessary for purposes of analysis and the gait analysis apparatus 100 would only measure accelerations imposed on the sensor region 104 as detailed above with respect to the first exemplary embodiment. In addition to all the benefits and advantages discussed above for a system measuring accelerations, accelerometers generally have a much higher degree of overloading tolerance than load sensors. For example, a typical accelerometer can withstand twenty g's of force before failure, while load sensors can generally barely handle a couple hundred pounds of off-axis loading before failure.

Accordingly, as illustrated in FIGS. 10 and 11, a suspension assembly 910, 912 is provided as part of the limiting members 502, 602 for both the for-aft load sensor modules 901 and lateral load sensor modules 902. Each of the suspension assemblies 910, 912 are comprised of a pair of mounting brackets 920, a pair of wire-rope assemblies 928, a suspended holder 930, and coupling screw 932. Each of the wire-ropes assemblies 928 is comprised of a pair of inner and outer threaded ends 922, 926 affixed to the opposite ends of each of the flexible cable 924. The top of each of the mounting brackets 920 is affixed to the bottom of the floor plates 307 of the sensor region 104, and the sides of each of the mounting brackets 920 includes a hole 934 to hold the flexible cable 924 of each the wire-rope assemblies 928 through the sides of each of the mounting brackets 920. The flexible cable 924 is preferably a string, wire, rope, cable, chain, etc., which is composed of preferably nylon, metal, natural fibers, etc. As with the flexible link 402 provided as part of the vertical load sensor modules 301, the required degree of flexibility and strength for flexible cable 924 depends on the forces and/or accelerations being applied to the floor plates 301 by the test subject.

The inner threaded ends 926 of each of the wire-rope assemblies 928 press on opposite sides of the suspended holder 930, and, in conjunction, the outer threaded ends 922 pull on the sides of each of the mounting brackets 920. Accordingly, the pair of wire-rope assemblies 928 holds the suspended holder 930 in tension between the pair of mounting brackets 920 via the pair of flexible cables 924, consequently limiting freedom of movement of the sensor region 104 to move a limited amount of distance while remaining suspended in all directions. Specifically, as discussed above in regards to FIG. 10, the coupling screw 932 attaches the load sensors 503, 504 to the moveable suspended holder 930 such that the suspended holder 930 is permitted to move a limited amount of distance between each of the wire-rope assemblies 928 causing each of the for-aft and lateral load sensors 503, 603 to measure the loads applied in its respective direction. For example, each of the floor plates 307 of the sensor region 104 are suspended in the lateral and for-aft directions by a pair of wire-rope assemblies 928 restricting movement for a limited amount in the lateral and for-aft directions to provide a stable sensor platform for the test subject to traverse and reducing any effects of friction and/or any chances of misalignment caused by continued use of the system. Accordingly, the accuracy of the results (e.g., recordation of measurements by the load sensors 403, 503, 603 and accelerometers 702) is greatly improved as well as the overall durability of the gait analysis apparatus 100.

One of the exemplary advantages of suspension assembly 910, 912 is that the sensor region 104 is suspended in suspended in all three directions, not only from the vertical load sensor module 301 but also the lateral load sensor modules 903 and for-aft load sensor modules 902, further reducing any interference possibilities from friction forces and providing more precise and reliable data for purposes of modeling and diagnosis. Further, by fixing the load sensors 503, 603 static such that any off-axis load applied merely bends the flexible cable 924, the suspension assemblies 910, 912 advantageously reduce chances of damage of the for-aft and lateral load sensors 503, 603. Please note that the same suspension configuration shown in FIG. 11 is applicable to both for-aft load sensor modules 910 and lateral load sensor modules 912. In addition, the configuration depicted in FIG. 11 simplifies maintenance of the gait analysis apparatus 100 and replacement of critical components (e.g., replacement of the fixed load sensors 503, 603). In contrast to suspending the sensor region 104 in only one direction (e.g., the vertical or Z direction and limiting the sensor region 104 from movement in the other directions from which it is not suspended (e.g., lateral or X direction and for-aft or Y direction, the sensor region 104 is suspended in all three directions. The novel suspension in all three directions (X, Y and Z) enhances the structural stability of the sensor region 104 and it eliminates the play and eventual system failure that was displayed after larger test subjects (e.g., cows) walk over the system for an extended period of time (e.g., 2-3 months).

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Various embodiments disclosed herein are described as including a particular feature, structure, or characteristic, but every aspect or embodiment may not necessarily include the particular feature, structure, or characteristic. Further, when a particular feature, structure, or characteristic is described in connection with an embodiment, it will be understood that such feature, structure, or characteristic may be included in connection with other embodiments, whether or not explicitly described. Thus, various changes and modifications may be made to the provided description without departing from the scope or spirit of the disclosure.

Other embodiments, uses and features of the present disclosure will be apparent to those skilled in the art from consideration of the specification and practice of the inventive concepts disclosed herein. The specification and drawings should be considered exemplary only.

What is claimed is:

1. A gait analysis apparatus configured to monitor locomotion comprising:
   a sensor region suspended in a plurality of directions selected from a first group consisting of vertical, fore-aft, and lateral directions;
   a load sensor module comprising one or more load sensors, wherein the load sensor module is configured to measure loads generated by a first test subject traversing the sensor region;
   a flexible link configured to suspend the sensor region from the load sensor module in only one of the plurality of directions;
   at least one pair of limiting members positioned on opposite sides of the one or more load sensors such that the apparatus comprises a single pair of limiting members for each load sensor and such that each limiting member within the pair of limiting members is positioned on opposite sides of a single load sensor, wherein the at least one pair of limiting members includes a suspension assembly to suspend the sensor region from the load sensor module in at least one of the plurality of directions different from a suspension direction of the sensor region by the flexible link, wherein the at least one pair of limiting members are configured to permit the sensor region to move a limited amount of distance relative to the load sensor module, wherein movement of the limited amount of distance by the sensor region causes the load sensor module to measure the loads in at least one of the plurality of directions different from the suspension direction of the sensor region by the flexible link, wherein the load sensor module is configured to measure the loads in each of the at least one of the plurality of directions different from the suspension direction and to provide each of the respective measurements of the loads to be processed.

2. The gait analysis apparatus of claim 1, wherein the at least one pair of limiting members are coupled to the sensor region and configured to move with the sensor region to limit movement of the sensor region relative to the load sensor module, wherein movement of the at least one pair of limiting members causes the load sensor module to measure the loads in at least one of the plurality of directions different from the suspension direction of the sensor region by the flexible link.

3. The gait analysis apparatus of claim 2, wherein the suspension assembly comprises:
   a pair of wire-rope assemblies that each include an inner threaded end and an outer threaded end affixed to opposite ends of a flexible cable; and
   a mounting bracket coupled to the bottom of the sensor region, wherein the mounting bracket includes a hole to hold the flexible cable of each of the pair of wire-rope assemblies,
   wherein the inner threaded end of each of the each of the pair of wire-rope assemblies presses on opposite sides of a suspended holder, and wherein the outer threaded end of the pair of wire-rope assemblies pulls on the sides of each of the mounting bracket.

4. The gait analysis apparatus of claim 3, wherein the suspension assembly includes a coupling screw to attach the one or more load sensors to the suspended holder, wherein the suspended holder is coupled to the sensor region and configured to move with the sensor region to limit movement of the sensor region relative to the load sensor module, wherein movement of the suspended holder causes the load sensor module to measure the loads in at least one of the plurality of directions different from the suspension direction of the sensor region by the flexible link.

5. The gait analysis apparatus of claim 1, wherein each of the one or more load sensors are coupled to the sensor region and configured to move with the sensor region the limited amount of distance between its respective pair of limiting members.

6. The gait analysis apparatus of claim 1, wherein the one or more load sensors of the load sensor module comprises:
   at least one fore-aft load sensor coupled to the sensor region, wherein the at least one fore-aft load sensor is configured to detect a fore-aft load on the sensor region and to generate one or more fore-aft load measurements in response to the detected fore-aft load; and
   at least one lateral load sensor coupled to the sensor region, wherein the at least one lateral load sensor is configured to detect a lateral load on the sensor region and to generate one or more lateral load measurements in response to the detected lateral load,
   wherein the at least one fore-aft load sensor is configured to provide the one or more fore-aft load measurements to be processed, wherein the at least one lateral load sensor is configured to provide the one or more lateral load measurements to be processed.

7. The gait analysis apparatus of claim 6, wherein the one or more load sensors of the load sensor module comprises:
   at least one vertical load sensor coupled to the sensor region, wherein the at least one vertical load sensor is configured to detect a vertical load on the sensor region and to generate one or more vertical load measurements in response to the detected vertical load,
   wherein the at least one vertical load sensor is configured to provide the one or more vertical load measurements to be processed.

8. The gait analysis apparatus of claim 1, wherein the one or more load sensors of the load sensor module comprises:
   at least one fore-aft load sensor coupled to the sensor region, wherein the at least one fore-aft load sensor is configured to detect a fore-aft load on the sensor region and to generate one or more fore-aft load measurements in response to the detected fore-aft load; and
   at least one vertical load sensor coupled to the sensor region, wherein the at least one vertical load sensor is configured to detect a vertical load on the sensor region and to generate one or more vertical load measurements in response to the detected vertical load;

wherein the at least one fore-aft load sensor is configured to provide the one or more fore-aft load measurements to be processed, wherein the at least one vertical load sensor is configured to provide the one or more vertical load measurements to be processed.

9. The gait analysis apparatus of claim 1, wherein the one or more load sensors of the load sensor module comprises a plurality of load sensors, which includes:

at least one vertical load sensor coupled to the sensor region, wherein the at least one vertical load sensor is configured to detect a vertical load on the sensor region and to generate one or more vertical load measurements in response to the detected vertical load; and at least one lateral load sensor coupled to the sensor region, wherein the at least one lateral load sensor is configured to detect a lateral load on the sensor region and to generate one or more lateral load measurements in response to the detected lateral load;

wherein the at least one vertical load sensor is configured to provide the one or more vertical load measurements to be processed, wherein the at least one lateral load sensor is configured to provide the one or more lateral load measurements to be processed.

10. The gait analysis apparatus of claim 1, wherein the one or more load sensors of the load sensor module comprises:

a plurality of single-axis load sensors selected from a second group consisting of at least one fore-aft load sensor configured to measure the loads in the fore-aft direction, at least one lateral load sensor configured to measure the loads in the lateral direction, and at least one vertical load sensor configured to measure the loads in the vertical direction, wherein each one of the plurality of single-axis load sensors is configured to provide each of the respective measurements of the loads to be processed.

11. The gait analysis apparatus of claim 1, wherein the sensor region comprises a first floor plate and a second floor plate that are disposed adjacently to one another, wherein the first floor plate is configured to be moved independently of the second floor plate.

12. The gait analysis apparatus of claim 11, wherein the first floor plate and the second floor plate are each coupled to a respective load sensor module.

13. The gait analysis apparatus of claim 11, wherein the first floor plate and the second floor plate are rectangular.

14. The gait analysis apparatus of claim 1, wherein the gait analysis apparatus includes a gait measuring processing device which receives the respective measurements of the loads to be processed, the gait measuring processing device comprising one or more processors programmed to implement instructions to:

receive at least two types of first load measurements associated with a first type of locomotion of the first test subject;

generate a first plurality of locomotion parameters (LPs) based on the at least two types of first load measurements;

generate a probability model based on the first plurality of LPs;

upon generating the probability model, receive at least two types of second load measurements associated with a second type of locomotion of a second test subject;

generate a second plurality of LPs based on the at least two types of second load measurements and corresponding to the first plurality of LPs;

compare each one of the first plurality of LPs with each one of the corresponding second plurality of LPs based on the probability model; and determine a plurality of biomarkers that predict one of the types of locomotion based on the comparison.

15. The gait analysis apparatus of claim 14, wherein the at least two types of first load measurements are selected from a third group consisting of a vertical load measurement that measures a vertical load imposed by the first test subject, a lateral load measurement that measures a lateral load imposed by the first test subject, and a fore-aft load measurement that measures a fore-aft load imposed by the first test subject.

16. The gait analysis apparatus of claim 14, wherein the first type of locomotion is healthy locomotion and the second type of locomotion is impaired locomotion.

17. The gait analysis apparatus of claim 14, wherein the first type of locomotion is impaired locomotion and the second type of locomotion is healthy locomotion.

18. The gait analysis apparatus of claim 14, wherein the one or more processors are further programmed to implement instructions to:

upon determining the plurality of biomarkers, receive at least two types of third load measurements associated with a third type of locomotion of a third test subject;

generate a third plurality of LPs based on the at least two types of third load measurements corresponding to the plurality of biomarkers; and compare each of the plurality of biomarkers with each of the corresponding third plurality of LPs in order to diagnosis the third test subject, wherein the third type of locomotion of the third test subject is unknown.

19. The gait analysis apparatus of claim 1, wherein the flexible link is one of a string, a wire, a rope, a cable, or a chain.

20. A system for gait analysis comprising:

a gait measurement processing device;

a gait analysis apparatus operatively coupled to the gait measurement processing device, comprising:

a first floor plate and a second floor plate that are disposed adjacently to one another, wherein the first floor plate is configured to be moved independently of the second floor plate;

at least one vertical load sensor coupled to each of the first floor plate and the second floor plate, wherein the at least one vertical load sensor is configured to detect a vertical load on either or both of the first floor plate and the second floor plate and to generate one or more vertical load measurements in response to the detected vertical load;

a flexible link configured to suspend each of the first floor plate and the second floor plate in a vertical direction;

at least one fore-aft load sensor coupled to each of the first floor plate and the second floor plate, wherein the at least one fore-aft load sensor is configured to detect a fore-aft load on either or both of the first floor plate and the second floor plate;

at least one first pair of limiting members coupled to each of said first floor plate and said second floor plate configured to permit one or more of the first and second floor plates to move a limited amount of fore-aft distance of each of the first floor plate and the second floor plate, wherein movement of the limited amount of fore-aft distance by one or more of the first and second floor plates causes the at least one fore-aft load sensor to generate one or more fore-aft load measurements in response to the detected fore-aft load, wherein the at least one first pair of limiting members is positioned on opposite sides of the at least one fore-aft load sensor such that the apparatus comprises a single pair of limiting members for each fore-aft load sensor and such that each limiting member within the first pair of limiting members is positioned on opposite sides of a single fore-aft load sensor, wherein the at least one first pair of limiting members include a suspension assembly to suspend each of the first floor plate and the second floor plate in a fore-aft direction;

at least one lateral load sensor coupled to each of the first floor plate and the second floor plate, wherein the at least one lateral load sensor is configured to detect a lateral load on either or both of the first floor plate and the second floor plate;

at least one second pair of limiting members coupled to each of said first floor plate and said second floor plate configured to permit one or more of the first and second floor plates to move a limited amount of lateral distance of each of the first floor plate and the second floor plate, wherein movement of the limited amount of lateral distance by one or more of the first and second floor plates causes the at least one lateral load sensor to generate one or more lateral load measurements in response to the detected lateral load, wherein the at least one second pair of limiting members is positioned on opposite sides of the at least one lateral load sensor such that the apparatus comprises a single pair of limiting members for each lateral load sensor and such that each limiting member within the second pair of limiting members is positioned on opposite sides of a single lateral load sensor, wherein the at least one second pair of limiting members include a suspension assembly to suspend each of the first floor plate and the second floor plate in a lateral direction; and wherein the at least one vertical load sensor is configured to provide the one or more vertical load measurements to the gait measurement processing device, the at least one fore-aft load sensor is configured to provide the one or more fore-aft load measurements to the gait measurement processing device, and the at least one lateral load sensor is configured to provide the one or more lateral load measurements to the gait measuring processing device;

wherein the gait measurement processing device comprises one or more processors programmed to implement instructions to:

receive the vertical load measurements, the fore-aft load measurements, and the lateral load measurements;

generate a plurality of locomotion parameters (LPs) based on the received load measurements;

analyze the plurality of LPs; and generate a probability model based on the analysis.

\* \* \* \* \*